(12) United States Patent
  Slater et al.

(10) Patent No.: US 6,465,008 B1
(45) Date of Patent: Oct. 15, 2002

(54) LIPOSOME-ENTRAPPED TOPOISOMERASE INHIBITORS

(75) Inventors: James L. Slater, Palo Alto, CA (US); Gail T. Colbern, Pacifica, CA (US); Peter K. Working, Burlingame, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/046,326

(22) Filed: Oct. 19, 2001

Related U.S. Application Data

(63) Continuation of application No. 09/419,189, filed on Oct. 15, 1999, now Pat. No. 6,355,268.
(60) Provisional application No. 60/104,671, filed on Oct. 16, 1998.

(51) Int. Cl.$^7$ ................................................ A61K 9/127
(52) U.S. Cl. ...................................................... 424/450
(58) Field of Search .......................... 424/450; 514/283, 514/279

(56) References Cited

U.S. PATENT DOCUMENTS

| | | |
|---|---|---|
| 5,552,156 A | 9/1996 | Burke |
| 5,891,468 A | 4/1999 | Martin |

FOREIGN PATENT DOCUMENTS

| | | |
|---|---|---|
| WO | WO 94/26253 | 11/1994 |
| WO | WO 95/08986 | 4/1995 |
| WO | WO 98/17256 | 4/1998 |

OTHER PUBLICATIONS

Clements, M.K., et al., "Camptothecin exhibits selective cytotoxicity towards human breast carcinoma as compared to normal bovine endothelial cells in vitro" *Anti–cancer Drugs* 7:851–857 (1996).

Daoud, S.S., et al., "Antitumor effect of liposome–incorporated camptothecin in human malignant xenografts" *Anti–Cancer Drugs* 6:83–93 (1995).

Emerson, D.L., et al., "NX–211, A liposomal formulation of Lurtotecan demonstrates enhanced Pharmacokinetic and antitumor activity" *Proc. American Assoc. Cancer Research* 39:278 (1998) (abstract #1897).

Lundberg, B.B., "Biologically active camptothecin derivatives for incorporation into liposome bilayers and lipid emulsions" *Anti–Cancer Drug Design* 13:453–461 (1998).

(List continued on next page.)

Primary Examiner—Gollamudi S. Kishore
(74) Attorney, Agent, or Firm—Paul B. Simboli; Judy M. Mohr

(57) ABSTRACT

A composition for administration of a therapeutically effective dose of a topoisomerase inhibitor I or topoisomerase I/II inhibitor is described. The composition includes liposomes having an outer surface and an inner surface defining an aqueous liposome compartment, and being composed of a vesicle-forming lipid and of a vesicle-forming lipid derivatized with a hydrophilic polymer to form a coating of hydrophilic polymer chains on both the inner and outer surfaces of the liposomes. Entrapped in the liposomes is the topoisomerase inhibitor at a concentration of at least about 0.10 µmole drug per µmole lipid.

57 Claims, 7 Drawing Sheets

OTHER PUBLICATIONS

Lynam, E., et al., "Camptothecin analogue efficacy in vitro: Effect of liposomal encapsulation of GI147211C (Lurtotecan) on in vitro cytotoxicity for multiple tumor cell types" *Proc. American Assoc. Cancer Research* 39:421 (1998) (abstract #2863).

Madden, T.D., et al., "Encapsulation of topotecan in lipid–based carrier systems. Evaluation of drug stability and plasma elimination in a murine model, and comparison of antitumor efficacy against murine L1210 and B16 tumors" *Proc. of ASCO* 17:abstract #754 (1998).

Subramanian, D., and Muller, M.T., "Liposomal Encapsulation Increases the Activity of the Topoisomerase I Inhibitor Topotecan" *Oncology Research* 7(9):461–469 (1995).

Sadzuka, Y., et al., "Effect of liposomalization on the antitumor activity, side–effects and tissue distribution of CPT–11" Cancer Letters 127:99–106 (1998).

Zhu, G., et al., "The effect of vincristine–polyanion complexes in Stealth liposomes on pharmacokinetics, toxicity and anti tumor activity" *Cancer Chemother Pharmacol* 39:138–142 (1996).

LIPOSOME-ENTRAPPED TOPOISOMERASE INHIBITORS

This application is a continuation of U.S. application Ser. No. 09/419,189 filed Oct. 15, 1999, now U.S. Pat. No. 6,355,268, which claims the benefit of U.S. Provisional Application No. 60/104,671 filed Oct. 16, 1998, both of which are incorporated herein by reference in their entirety.

FIELD OF THE INVENTION

The present invention relates to a liposome composition having an entrapped topoisomerase inhibitor.

BACKGROUND OF THE INVENTION

Next to heart disease, cancer is the major cause of death in the United States, causing over 500,000 fatalities annually (Katzung, B., "Basic and Clinical Pharmacology", $7^{th}$ Edition, Appleton & Lange, Stamford Conn., 1998, p. 882). With present methods of treatment, one-third of patients are cured with local measures, such as surgery or radiation therapy, which are quite effective when the tumor has not metastasized by the time of treatment. Earlier diagnosis might lead to increased cure of patients undergoing such local treatments. However, in many cases, early micrometastasis is a characteristic feature of the neoplasm, indicating that a systemic approach such as chemotherapy may be required, often along with a local treatment method, for effective cancer management.

Cancer chemotherapy can be curative in certain disseminated neoplasms that have undergone either gross or microscopic spread by the time of diagnosis. These include testicular cancer, diffuse large cell lymphoma, Hodgkin's disease and choriocarcinoma as well as childhood tumors such as acute lymphoblastic leukemia. For other forms of disseminated cancer, chemotherapy provides a palliative rather than curative therapy. Effective palliative therapy results in temporary clearing of the symptoms and signs of cancer and prolongation of useful life. Advances in cancer chemotherapy have recently provided evidence that chemical control of neoplasia is possible for a number of cancers.

One category of drugs used for cancer therapy is topoisomerase inhibitors. These compounds inhibit the action of topoisomerase enzymes which play a role in the replication, repair, genetic recombination and transcription of DNA. An example of a topoisomerase inhibitor is camptothecin, a natural compound that interferes with the activity of topoisomerase I, an enzyme involved in DNA replication and RNA transcription. Camptothecin and the camptothecin analogues topotecan and irinotecan are approved for clinical use.

Camptothecin and its analogues are effective in cancer chemotherapy by interfering with the breakage/reunion actions of topoisomerase I. The compounds stabilize and form a reversible enzyme-camptothecin-DNA ternary complex which prevents the reunion step of the breakage/union cycle of the topoisomerase reaction.

One problem with camptothecin is its water insolubility, which hinders the delivery of the drug. Numerous analogues of camptothecin have been prepared to improve the compound's water solubility. Another problem with camptothecin and its analogues is that the compounds are susceptible in aqueous environments to hydrolysis at the α-hydroxy lactone ring. The lactone ring opens to the carboxylate form of the drug, a form that exhibits little activity against topoisomerase I.

Various approaches to improving the stability of camptothecin and its analogues have been described. One approach has been to entrap the compounds in liposomes. Burke (U.S. Pat. No. 5,552,156) describes a liposome composition intended to overcome the instability of camptothecin and its analogues by entrapping the compounds in liposomes having a lipid bilayer membrane which allows the compound to penetrate, or intercalate, into the lipid bilayer. With the compound intercalated into the bilayer membrane, it is removed from the aqueous environment in the core of the liposome and thereby protected from hydrolysis.

One problem with this approach is that the liposomes are quickly removed from the bloodstream by the reticuloendothelial system (RES), preventing delivery, and preferably accumulation, at the tumor site.

Subramanian and Muller (*Oncology Research*, 7(9) :461–469 (1995)) describe a liposome formulation of topotecan and report that in liposome-entrapped form, topotecan is stabilized from inactivation by hydrolysis of the lactone ring. However, the biological activity of the liposome-entrapped drug in vitro has only 60% of the activity of the free drug.

Lundberg (*Anti-Cancer Drug Design*, 13:453 (1998)) describes two lipophilic, oleic acid ester derivatives of camptothecin analogues which are entrapped in liposomes and intercalated into the bilayer for stabilization of the lactone ring. Daoud (*Anti-Cancer Drugs*, 6:83–93 (1995)) describes a liposome composition including camptothecin, where the drug is also intercalated into the lipid bilayer. The liposomes in both of these references are prepared conventionally, where the drug is passively entrapped in the liposomes to sequester the drug in the lipid bilayer membrane for stabilization. Using this method of preparation it is difficult to achieve a sufficient drug load in the liposomes for clinical efficacy.

Accordingly, there is still a need in the art for a liposome formulation which (i) includes a topoisomerase inhibitor, such as camptothecin and its analogues; (ii) remains in the bloodstream for a prolonged period of time; (iii) retains antitumor activity; and (iv) includes a sufficient drug load for clinical relevance.

SUMMARY OF THE INVENTION

Accordingly, it is an object of the invention to provide a topoisomerase inhibitor composition for improved cancer therapy.

It is another object of the invention to provide a liposome composition for administration of a topoisomerase inhibitor for antitumor therapy.

In one aspect, the invention includes a composition for treating a tumor in a subject, comprising liposomes composed of a vesicle-forming lipid and between about 1–20 mole percent of a vesicle-forming lipid derivatized with a hydrophilic polymer. The liposomes are formed under conditions that distribute the polymer on both sides of the liposomes' bilayer membranes. Entrapped in the liposomes is a topoisomerase I inhibitor or a topoisomerase I/II inhibitor at a concentration of at least about 0.10 μmole drug per μmole lipid. The liposomes have an inside/outside ion gradient sufficient to retain the topoisomerase I inhibitor or topoisomerase I/II inhibitor within the liposomes at the specified concentration.

In one embodiment, the topoisomerase inhibitor is a topoisomerase I inhibitor selected from the group consisting of camptothecin and camptothecin derivatives. For example, the camptothecin derivative can be 9-aminocamptothecin, 7-ethylcamptothecin, 10-hydroxycamptothecin, 9-nitrocamptothecin, 10,11-methlyenedioxycamptothecin, 9-amino-10,11-methylenedioxycamptothecin or 9-chloro- 10,11-methylenedioxycamptothecin. In other embodiments, the camptothecin derivative is irinotecan, topotecan, (7-(4-methylpiperazinomethylene)-10,11-ethylenedioxy-20(S)-camptothecin, 7-(4-methylpiperazinomethylene)-10,11-methylenedioxy-20(S)-camptothecin or 7-(2-(N-isopropylamino)ethyl)-(20S)-camptothecin.

In another embodiment, the topoisomerase inhibitor is a topoisomerase I/II inhibitor, such as 6-[[2-(dimethylamino)-ethyl]amino]-3-hydroxy-7H-indeno[2,1-c]quinolin-7-one dihydrochloride, azotoxin or 3-methoxy-11H-pyrido[3',4'-4,5]pyrrolo[3,2-c]quinoline-1,4-dione.

The hydrophilic polymer included in the liposome composition can be polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol and polyaspartamide.

In a preferred embodiment, the hydrophilic polymer is polyethyleneglycol having a molecular weight between 500–5,000 daltons.

In still another embodiment, the liposomes further include a vesicle-forming lipid having a phase transition temperature above 37° C.

In yet another embodiment, the vesicle-forming lipid is hydrogenated soy phosphatidylcholine, distearoyl phosphatidylcholine or sphingomyelin. One preferred liposome composition is composed of 20–94 mole percent hydrogenated soy phosphatidylcholine, 1–20 mole percent distearoyl phosphatidylcholine derivatized with polyethyleneglycol and 5–60 mole percent cholesterol.

Another preferred composition is 30–65 mole percent hydrogenated soy phosphatidylcholine, 5–20 mole percent distearoyl phosphatidylcholine derivatized with polyethyleneglycol and 30–50 mole percent cholesterol.

In another aspect, the invention includes a composition for administration of a topoisomerase I inhibitor or a topoisomerase I/II inhibitor, comprising liposomes composed of vesicle-forming lipids and having an inside/outside ion gradient effective to retain the drug within the liposomes. Entrapped in the liposomes is the topoisomerase I inhibitor or the topoisomerase I/II inhibitor at a concentration of at least about 0.20 μmole drug per μmole lipid.

In another aspect, the invention includes a method of treating a tumor in a subject, comprising preparing liposomes composed of vesicle-forming lipids including between 1–20 mole percent of a vesicle-forming lipid derivatized with a hydrophilic polymer chain, the liposomes being formed under conditions that distribute the polymer on both sides of the liposomes' bilayer membrane. The liposomes contain a topoisomerase I inhibitor or a topoisomerase I/II inhibitor entrapped in the liposomes at a concentration of at least about 0.10 mole per μmole lipid, the liposomes having an inside/outside ion gradient sufficient to retain the topoisomerase I inhibitor or topoisomerase I/II inhibitor within the liposome at the specified concentration. The liposomes are then administered to the subject.

In one embodiment of this aspect, the method further includes entrapping the topoisomerase I inhibitor or topoisomerase I/II inhibitor in the liposomes by remote loading, for example, via an ammonium sulfate gradient.

These and other objects and features of the invention will be more fully appreciated when the following detailed description of the invention is read in conjunction with the accompanying drawings.

DETAILED DESCRIPTION OF THE INVENTION

I. Definitions

Figure 1A:
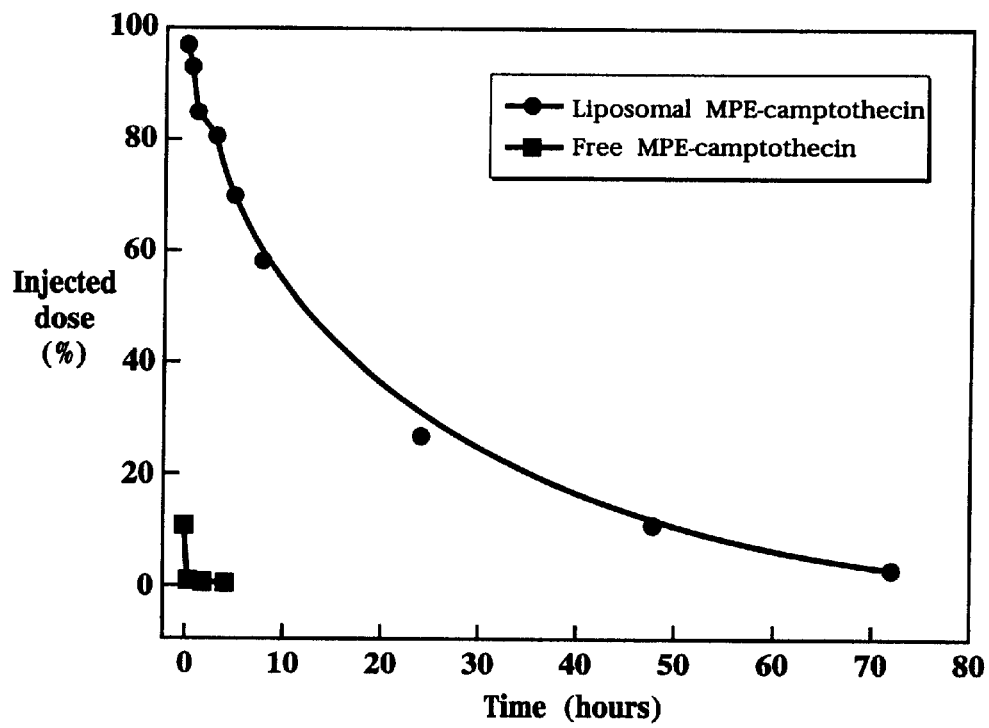
FIG. 1A is a plot of the blood circulation lifetime of liposome-entrapped MPE-camptothecin (solid circles), taken as the percent of injected dose as a function of time, compared to the free form of the drug (solid squares)

Unless otherwise indicated, the terms below have the following meaning:

"Effective amount" or "effective dose" refers to the amount necessary or sufficient to inhibit undesirable cell growth, e.g., prevent undesirable cell growth or reduce existing cell growth, such as tumor cell growth. The effective amount can vary depending on factors known to those of skill in the art, such as the type of cell growth, the mode and regimen of administration, the size of the subject, the severity of the cell growth, etc. One of skill in the art would be able to consider such factors and make the determination regarding the effective amount.

"Therapeutically effective antitumor therapy" refers to a therapy which is effective to maintain or decrease the size, e.g., volume, of a primary tumor or metastatic tumor.

"Topoisomerase I inhibitor" refers to any compound that inhibits or reduces the action of topoisomerase I enzyme.

"Topoisomerase I/II inhibitor" refers to any compound that inhibits or reduces the action of both topoisomerase I enzyme and topoisomerase II enzyme.

"Topoisomerase inhibitor" refers to a topoisomerase I inhibitor or a topoisomerase I/II inhibitor.

"MPE-camptothecin" refers to 7-(4-methyl-piperazino-methylene)-10,11-ethylenedioxy-20(S)-camptothecin.

"Topotecan" refers to 9-dimethyl-aminomethyl-10-hydroxycamptothecin.

"CKD-602" refers to 7-(2-(N-isopropylamino)ethyl)-(20S)-camptothecin.

II. Liposome Composition

The present invention is directed to a liposome composition for administration of a topoisomerase I inhibitor or a topoisomerase I/II inhibitor. In studies performed in support of the invention, three topoisomerase inhibitors were entrapped in liposomes and characterized in vivo: topotecan, 7-(4-methyl-piperazino-methylene)-10,11-ethylenedioxy-20(S)-camptothecin (referred to hereing as "MPE-camptothecin") and 7-(2-(N-isopropylamino)ethyl)-(20S)-camptothecin (referred to herein as "CKD-602"). The drugs were entrapped in liposomes by remote loading to achieve a high drug load stably retained in the liposomes, as will be described. In vivo studies with the formulations demonstrated that the liposome composition achieves a surprising and unexpected degree of improvement in therapeutic activity when compared to therapy with the topoisomerase inhibitor in free form. More specifically, and as will be described below, the dose of the liposome-entrapped topoisomerase I inhibitor MPE-camptothecin required to achieve therapeutic antitumor therapy is about 20 times lower than the dose required when the drug is administered in free form.

In this section, the liposome composition will be described, including methods for preparing the liposomes.

A. Liposome Components

Liposomes suitable for use in the composition of the present invention include those composed primarily of vesicle-forming lipids. Vesicle-forming lipids can form spontaneously into bilayer vesicles in water, as exemplified by the phospholipids. The liposomes can also include other lipids incorporated into the lipid bilayers, with the hydrophobic moiety in contact with the interior, hydrophobic region of the bilayer membrane, and the head group moiety oriented toward the exterior, polar surface of the bilayer membrane.

The vesicle-forming lipids are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Cationic lipids are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3 [N-(N',N'-dimethylaminoethane) carbamoly] cholesterol (DC-Chol); and dimethyldioctadecylammonium (DDAB).

The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

In another embodiment, the vesicle-forming lipid is selected to achieve a specified degree of fluidity or rigidity, to control the stability of the liposome in serum and to control the rate of release of the entrapped agent in the liposome.

Liposomes having a more rigid lipid bilayer, or a liquid crystalline bilayer, are achieved by incorporation of a relatively rigid lipid, e.g., a lipid having a relatively high phase transition temperature, e.g., above room temperature, more preferably above body temperature and up to 80° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature, more preferably, at or below body temperature.

Vesicle-forming lipids having a main phase transition temperatures from approximately 2° C.–80° C. are suitable for use as the primary liposome component of the present composition. In a preferred embodiment of the invention, a vesicle-forming lipid having a main phase transition temperature above about 37° C. is used as the primary lipid component of the liposomes. In another preferred embodiment, a lipid having a phase transition temperature between about 37–70° C. is used. By way of example, the lipid distearoyl phosphatidylcholine (DSPC) has a main phase transition temperature of 55.1° C. and the lipid hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NIST Standard Reference Database 34).

The liposomes also include a vesicle-forming lipid derivatized with a hydrophilic polymer. As has been described, for example in U.S. Pat. No. 5,013,556 and in WO 98/07409, which are hereby incorporated by reference, such a hydrophilic polymer provides a surface coating of hydrophilic polymer chains on both the inner and outer surfaces of the liposome lipid bilayer membranes. The outermost surface coating of hydrophilic polymer chains is effective to provide a liposome with a long blood circulation lifetime in vivo. The inner coating of hydrophilic polymer chains extends into the aqueous compartments in the liposomes, i.e., between the lipid bilayers and into the central core compartment, and is in contact with the entrapped compound after the compound is loaded via remote loading. As will be illustrated below, the liposome formulation having a surface coating of hydrophilic polymer chains distributed on the inner and outer liposome surfaces provides for a topoisomerase I inhibitor or topoisomerase I/II inhibitor composition where the compound is retained in the liposomes for improved therapeutic activity.

Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide. The polymers may be employed as homopolymers or as block or random copolymers.

A preferred hydrophilic polymer chain is polyethyleneglycol (PEG), preferably as a PEG chain having a molecular weight between 500–10,000 daltons, more preferably between 500–5,000 daltons, most preferably between 1,000–2,000 daltons. Methoxy or ethoxy-capped analogues of PEG are also preferred hydrophilic polymers, commercially available in a variety of polymer sizes, e.g., 120–20, 000 daltons.

Preparation of vesicle-forming lipids derivatized with hydrophilic polymers has been described, for example in U.S. Pat. No. 5,395,619. Preparation of liposomes including such derivatized lipids has also been described, where typically, between 1–20 mole percent of such a derivatized lipid is included in the liposome formulation. It will be appreciated that the hydrophilic polymer may be stably coupled to the lipid, or coupled through an unstable linkage which allows the coated liposomes to shed the coating of polymer chains as they circulate in the bloodstream or in response to a stimulus.

B. Topoisomerase Inhibitor

The liposomes of the invention include a topoisomerase inhibitor entrapped in the liposome. Entrapped is intended to include encapsulation of an agent in the aqueous core and aqueous spaces of liposomes. It will be appreciated that for compounds having some hydrophobicity, entrapment in the lipid bilayer(s) of the liposomes may also occur.

Topoisomerases catalyze the introduction and relaxation of superhelicity in DNA. Several types of enzymes with varying specifities are known to be important in the replication of DNA, as well as in the repair, genetic recombination and transcription of DNA. The simplest topoisomerases, designated topoisomerase I, relax superhelical DNA, a process that is energetically spontaneous. The gyrases, which are known as topoisomerase II, catalyze the energy-requiring and ATP-dependent introduction of negative superhelical twists into DNA. In DNA replication, topoisomerases I and II have the function of relaxing the positive superhelicity that is introduced ahead of the replicating forks by the action of helicases. In addition, gyrases introduce negative twists into segments of DNA that allow single-strand regions to appear.

Topoisomerase inhibitors, then, are compounds that inhibit topoiosmerase activity. Compounds known as topoisomerase I inhibitors have activity against topoisomerase I, and the topoiosmerase II inhibitors have activity against topoisomerase II. Some compounds have activity against both topoisomerase I and topoisomerase II and are known as topoisomerase I/II inhibitors.

Preferred topoisomerase I inhibitors for use in the present invention are camptothecin and analogs of camptothecin. Camptothecin is a pentacyclic alkaloid initially isolated from the wood and bark of *Camptotheca acuminata,* a tree indigenous to China (Wall, M.E. et al., *J. Am. Chem. Soc.,* 94:388 (1966)). Camptothecin exerts its pharmacological effects by irreversibly inhibiting topoisomerase I. Methods for the synthesis of camptothecin and camptothecin analogs or derivatives are known, and are summarized and set forth in U.S. Pat. No. 5,244,903, which is herein incorporated by reference in its entirety.

Analogues of camptothecin include SN-38 ((+)-(4S)-4, 11-diethyl-4,9-dihydroxy-1H-pyrano[3',4':6,7]-indolizino [1,2-b]quinoline-3,14(4H,12H)-dione); 9-aminocamptothecin; topotecan (hycamtin; 9-dimethyl-aminomethyl-10-hydroxycamptothecin); irinotecan (CPT- 11; 7-ethyl-10-[4-(1-piperidino)-1-piperidino]-carbonyloxy-camptothecin), which is hydrolyzed in vivo to SN-38); 7-ethylcamptothecin and its derivatives (Sawada, S. et al., *Chem. Pharm. Bull.*, 41(2):310–313 (1993)); 7-chloromethyl-10,11-methylene-dioxy-camptothecin; and others (SN-22, Kunimoto, T. et al., *J. Pharmacobiodyn.*, 10(3):148–151 (1987); N-formylamino-12,13,dihydro-1,11-dihydroxy-13-(beta-D-glucopyranosyl)-5H-indolo[2,3-a] pyrrolo[3,4-c]carbazole-5,7(6H)-dione (NB-506, Kanzawa, F et al., *Cancer Res.*, 55(13):2806–2813 (1995); DX-8951f and lurtotecan (GG-211 or 7-(4-methylpiperazino-methylene)-10,11-ethylenedioxy-20(S)-camptothecin) (Rothenberg, M. L., *Ann. Oncol.*, 8(9) :837–855 (1997)) and 7-(2-(N-isopropylamino)ethyl)-(20S)-camptothecin (CKD602, Chong Kun Dang Corporation, Seoul Korea).

Topoisomerase inhibitors having activity against both topoisomerase I and topoisomerase II include 6-[[2-(dimethylamino)-ethyl]amino]-3-hydroxy-7H-indeno[2,1-c]quinolin-7-one dihydrochloride, (TAS-103, Utsugi, T., et al., *Jpn. J. Cancer Res.*, 88(10) :992–1002 (1997)) and 3-methoxy-11H-pyrido[3',4'-4,5]pyrrolo[3,2-c]quinoline-1,4-dione (AzaIQD, Riou, J.F., et al., *Mol. Pharmacol.*, 40(5) :699–706 (1991)).

In one embodiment of the invention, the topoisomerase I inhibitor administered is the pharmacologically active enantiomer of a camptothecin analogue having a chiral center. The enantiomer can be resolved from the racemic mixture using techniques known to those of skill in the art.

C. Method of Preparing the Liposome Composition

The liposomes may be prepared by a variety of techniques, such as those detailed in Szoka, F., Jr., et al., *Ann. Rev. Biophys. Bioeng.* 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids and including a vesicle-forming lipid derivatized with a hydrophilic polymer are dissolved in a suitable organic solvent which is evaporated in a vessel to form a dried thin film. The film is then covered by an aqueous medium to form MLVs, typically with sizes between about 0.1 to 10 microns. Exemplary methods of preparing derivatized lipids and of forming polymer-coated liposomes have been described in co-owned U.S. Pat. Nos. 5,013,556, 5,631,018 and 5,395,619, which are incorporated herein by reference.

The therapeutic agent of choice can be incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside liposome ion gradient, termed remote loading. Other methods, such as reverse evaporation phase liposome preparation, are also suitable.

In the present invention, a preferred method of preparing the liposomes is by remote loading. In the studies performed in support of the invention, three exemplary topoisomerase I inhibitors were loaded into pre-formed liposomes by remote loading against an ion concentration gradient, as has been described in the art (U.S. Pat. No. 5,192,549) and as described in Example 1. In a remote loading procedure, a drug is accumulated in the liposomes' central compartment at concentration levels much greater than can be achieved with other loading methods. In a preferred embodiment of the invention, the topoisomerase I inhibitor or topoisomerase I/II inhibitor is loaded into the liposomes to a concentration of at least about 0.10 μmole drug per μmole lipid, more preferably of at least about 0.15 μmole drug per μmole lipid, most preferably of at least about 0.20 μmole drug per μmole lipid. The liposomes prepared in support of the invention contained MPE-camptothecin, topotecan or CKD602. As set forth in Example 1, these compounds were loaded into the liposomes by remote loading, discussed below, to a drug concentration level of greater than 0.20 μmole drug per μmole lipid (see the table in Example 1).

Liposomes having an ion gradient across the liposome bilayer for use in remote loading can be prepared by a variety of techniques. A typical procedure is as described above, where a mixture of liposome-forming lipids is dissolved in a suitable organic solvent and evaporated in a vessel to form a thin film. The film is then covered with an aqueous medium containing the solute species that will form the aqueous phase in the liposome interior spaces.

After liposome formation, the vesicles may be sized to achieve a size distribution of liposomes within a selected range, according to known methods. The liposomes are preferably uniformly sized to a selected size range between 0.04 to 0.25 μm.

Small unilamellar vesicles (SUVs), typically in the 0.04 to 0.08 μm range, can be prepared by extensive sonication or homogenization of the liposomes. Homogeneously sized liposomes having sizes in a selected range between about 0.08 to 0.4 microns can be produced, e.g., by extrusion through polycarbonate membranes or other defined pore size membranes having selected uniform pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane. The sizing is preferably carried out in the original lipid-hydrating buffer, so that the liposome interior spaces retain this medium throughout the initial liposome processing steps.

After sizing, the external medium of the liposomes is treated to produce an ion gradient across the liposome membrane, which is typically a lower inside/higher outside concentration gradient. This may be done in a variety of ways, e.g., by (i) diluting the external medium, (ii) dialysis against the desired final medium, (iii) molecular-sieve chromatography, e.g., using Sephadex G-50, against the desired medium, or (iv) high-speed centrifugation and resuspension of pelleted liposomes in the desired final medium. The external medium which is selected will depend on the mechanism of gradient formation and the external pH desired, as will now be considered.

In the simplest approach for generating an ion gradient, the hydrated, sized liposomes have a selected internal-medium pH. The suspension of the liposomes is titrated until a desired final pH is reached, or treated as above to exchange the external phase buffer with one having the desired external pH. For example, the original medium may have a pH of 5.5, in a selected buffer, e.g., glutamate or phosphate buffer, and the final external medium may have a pH of 8.5 in the same or different buffer. The internal and external media are preferably selected to contain about the same osmolarity, e.g., by suitable adjustment of the concentration of buffer, salt, or low molecular weight solute, such as sucrose.

In another general approach, the gradient is produced by including in the liposomes, a selected ionophore. To illustrate, liposomes prepared to contain valinomycin in the liposome bilayer are prepared in a potassium buffer, sized, then exchanged with a sodium buffer, creating a potassium inside/sodium outside gradient. Movement of potassium ions in an inside-to-outside direction in turn generates a lower inside/higher outside pH gradient, presumably due to movement of protons into the liposomes in response to the net electronegative charge across the liposome membranes (Deamer, et al., 1972).

In another more preferred approach, the proton gradient used for drug loading is produced by creating an ammonium ion gradient across the liposome membrane, as described, for example, in U.S. Pat. No. 5,192,549. Here the liposomes are prepared in an aqueous buffer containing an ammonium salt, typically 0.1 to 0.3 M ammonium salt, such as ammonium sulfate, at a suitable pH, e.g., 5.5 to 7.5. The gradient can also be produced by using sulfated polymers, such as dextran ammonium sulfate or heparin sulfate. After liposome formation and sizing, the external medium is exchanged for one lacking ammonium ions, e.g., the same buffer but one in which ammonium sulfate is replaced by NaCl or a sugar that gives the same osmolarity inside and outside of the liposomes.

After liposome formation, the ammonium ions inside the liposomes are in equilibrium with ammonia and protons. Ammonia is able to penetrate the liposome bilayer and escape from the liposome interior. Escape of ammonia continuously shifts the equilibrium within the liposome toward the right, to production of protons.

The topoisomerase inhibitor is loaded into the liposomes by adding the drug to a suspension of the ion gradient liposomes, and the suspension is treated under conditions effective to allow passage of the compound from the external medium into the liposomes. Incubation conditions suitable for drug loading are those which (i) allow diffusion of the derivatized compound, with such in an uncharged form, into the liposomes, and (ii) preferably lead to high drug loading concentration, e.g., 5–500 mM drug encapsulated, more preferably between 20–200 mM, most preferably between 50–300 mM.

The loading is preferably carried out at a temperature above the phase transition temperature of the liposome lipids. Thus, for liposomes formed predominantly of saturated phospholipids, the loading temperature may be as high as 60 C. or more. The loading period is typically between 15–120 minutes, depending on permeability of the drug to the liposome bilayer membrane, temperature, and the relative concentrations of liposome lipid and drug.

With proper selection of liposome concentration, external concentration of added compound, and the ion gradient, essentially all of the compound may be loaded into the liposomes. For example, with a pH gradient of 3 units (or the potential of such a gradient employing an ammonium ion gradient), the final internal:external concentration of drug will be about 1000:1. Knowing the calculated internal liposome volume, and the maximum concentration of loaded drug, one can then select an amount of drug in the external medium which leads to substantially complete loading into the liposomes.

Alternatively, if drug loading is not effective to substantially deplete the external medium of free drug, the liposome suspension may be treated, following drug loading, to remove non-encapsulated drug. Free drug can be removed, for example, by molecular sieve chromatography, dialysis, or centrifugation.

In another embodiment of the invention, the topoisomerase inhibitor is loaded into preformed liposomes which include in the liposome interior a trapping agent effective to complex with the topoisomerase inhibitor and enhance retention of the compound. In a preferred embodiment, the trapping agent is a polyanionic polymer, e.g., a molecule consisting of repetitive units of preferably similar chemical structure and having ionizable groups, that is, chemical functional groups capable of electrolytic dissociation resulting in the formation of ionic charge, and preferably an anionic charge. Polymers having a molecular weight over a broad range are suitable, from 400–2,000,000 Daltons.

The polyanionic polymer is entrapped in the liposomes during lipid vesicle formation. Upon loading of a drug into the pre-formed liposomes, the polymer serves to trap or retain the drug within the liposomes. In the studies described herein, dextran sulfate was used as an exemplary polyanionic polymer. Dextran sulfate is a polymer of anhydroglucose with approximately 2.3 sulfate groups per glucosoyl residue. It is composed of approximately 95% alpha-D-1–6) linkages and the remaining (1–3) linkages account for the branching of dextran. The polymer is readily available in molecular weights ranging from 5,000 to 500,000 Daltons. However, other polymers are suitable including sulfated, sulfonated, carboxylated or phosphated hydrophilic polymers. For example, sulfated proteoglycans, such as sulfated heparin, sulfated polysaccharids, such as sulfated cellulose or cellulose derivatives, carrageenin, mucin, sulfated polypeptides, such as polylysine with sulfated amine groups, glycopeptides with sulfonate-derivatized saccharide or peptide subunits, and hyaluronic acid. Chondroitin sulfates A, B and C, keratin sulfates, dermatan sulfates are also contemplated. The polymer can also be a neutral polymer modified to include an anionic functional group. For example, amylose, pectin, amylopectin, celluloses, and dextran can be modified to include an anionic subunit. Polymers bearing a sulfo group such as polyvinylsulfate, polyvinylsulfonate polystyrenesulfonate and sulfated rosin gum are also suitable.

Preparation of liposomes which include such a trapping agent is described with respect to Example 4. In this example, the polyanionic polymer dextran sulfate is entrapped in the liposomes by adding the liposome lipids, which are first dissolved in ethanol, to a solution of dextran sulfate ammonium salt and mixed to form liposomes having dextran sulfate ammonium salt entrapped within the liposomes. The external media was exchanged to establish an ammonium ion gradient across the liposomes for remote loading of drug.

III. In Vivo Administration of the Composition

Liposomes were prepared in support of the invention as described in Example 1. The topoisomerase I inhibitors (7-(4-methylpiperazino)-methylene)-10,11-ethylenedioxy-20(S)-camptothecin), referred to herein as "MPE-camptothecin"; topotecan; and 7-(2-(N-isopropylamino) ethyl)-(20S)-camptothecin, referred to herein as "CKD-602", were loaded into liposomes under an ammonium sulfate ion concentration gradient. The liposomes were composed of hydrogenated soy phosphatidylcholine, cholesterol and polyethylene glycol derivatized to distearoyl phosphatidylethanolamine (PEG-DSPE) in a molar ratio 55.4:39:5.6. The table in Example 1 summarizes the drug to lipid ratios for the liposome formulations prepared. The calculated liposomal drug concentrations for the three compounds, based on an extruded liposome captured volume of 0.9 $\mu l/\mu mole$ lipid, are 284 mM for MPE-camptothecin, 264 mM for topotecan and 298 for CKD-602. Based on an extruded liposome captured volume of 1.5

µl/µmole lipid, the calculated liposomal drug concentrations are 189 mM for MPE-camptothecin, 174 mM for topotecan and 198 for CKD-602. The in vivo studies performed with each drug will now be described.

1. In Vivo Administration of MPE-Camptothecin

The long-circulating, PEG-coated liposomes containing MPE-camptothecin were administered to rats to determine the blood circulation lifetime of the drugs in liposome-entrapped form. The pharmacokinetic profile of the liposome-entrapped drug and of the free drug are shown in FIG. 1A as the percent of injected dose as a function of time. As can be seen, the blood circulation time of the topoisomerase I inhibitor in liposome-entrapped form (solid circles) is significantly longer than the free form of the drug (solid squares). For MPE-camptothecin, the blood circulation half-life of the liposome-entrapped drug was 14 hours, compared to about 50 minutes for the free drug. The blood clearance of the liposome-entrapped drug in rats was approximately 35-fold lower and the area under the curve was approximately 1250-fold higher than that of the free drug. Analytical results indicate that essentially all the drug remains entrapped in the liposomes in the bloodstream.

Figure 1B:
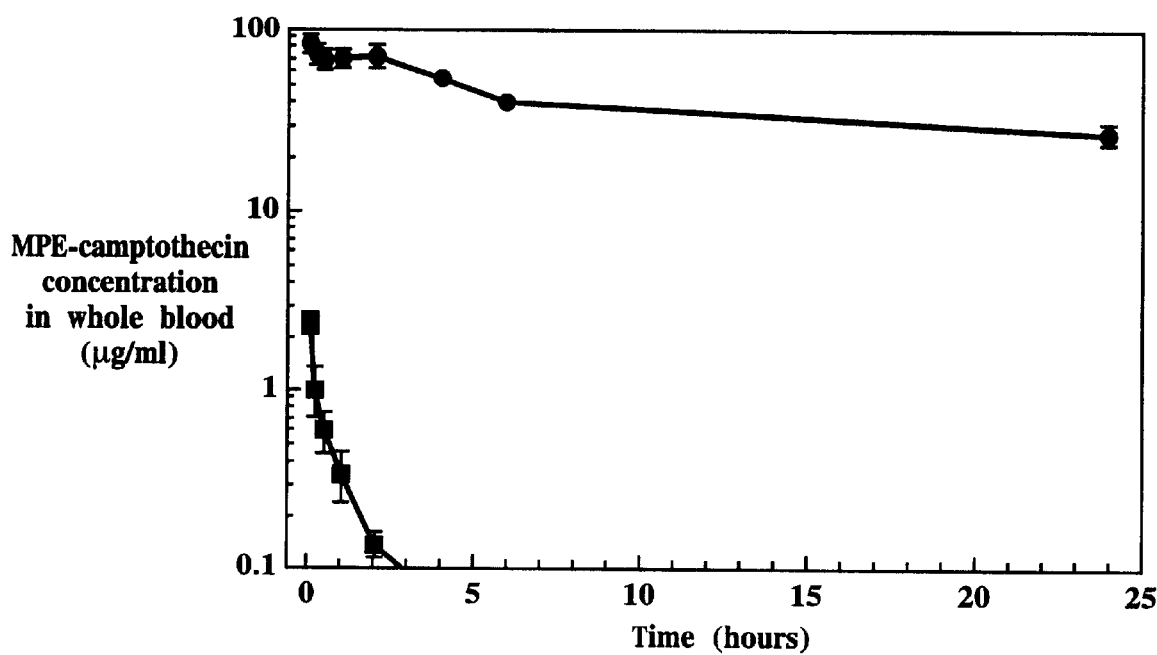
FIG. 1B shows the blood concentration of MPE-camptothecin, as a function of time, in hours, after administration of liposome-entrapped MPE-camptothecin (solid circles) and of free (non-liposomal) MPE-camptothecin (solid squares) to rats.

FIG. 1B shows the concentration of MPE-camptothecin in whole blood after administration of the liposome formulation (solid circles) and of the free drug to rats. The longer circulation lifetime results in a higher concentration of the drug in the blood.

The anti-tumor efficacy of the MPE-camptothecin liposome formulation was determined in xenograft tumor models, where homozygous nude mice were inoculated with human tumor cells of colon, HT29 origin. Surprisingly, these toxicity and antitumor efficacy studies showed that liposomal MPE-camptothecin was significantly more toxic than the free form of the drug at equivalent doses. These studies and the results will now be described.

Liposomes were prepared as set forth in Example 1 to include entrapped MPE-camptothecin. Nude mice with HT-29 colon xenografts were treated with liposome-entrapped MPE-camptothecin at dosages of 24 mg/kg, 15 mg/kg and 6 mg/kg or with free MPE-camptothecin at the same dosages. Treatment began 10 days after tumor inoculation and doses were administered at days 10, 16 and 23. The tumor volume in each animal was assessed during and following treatment as described in Example 2.

Figure 2A:
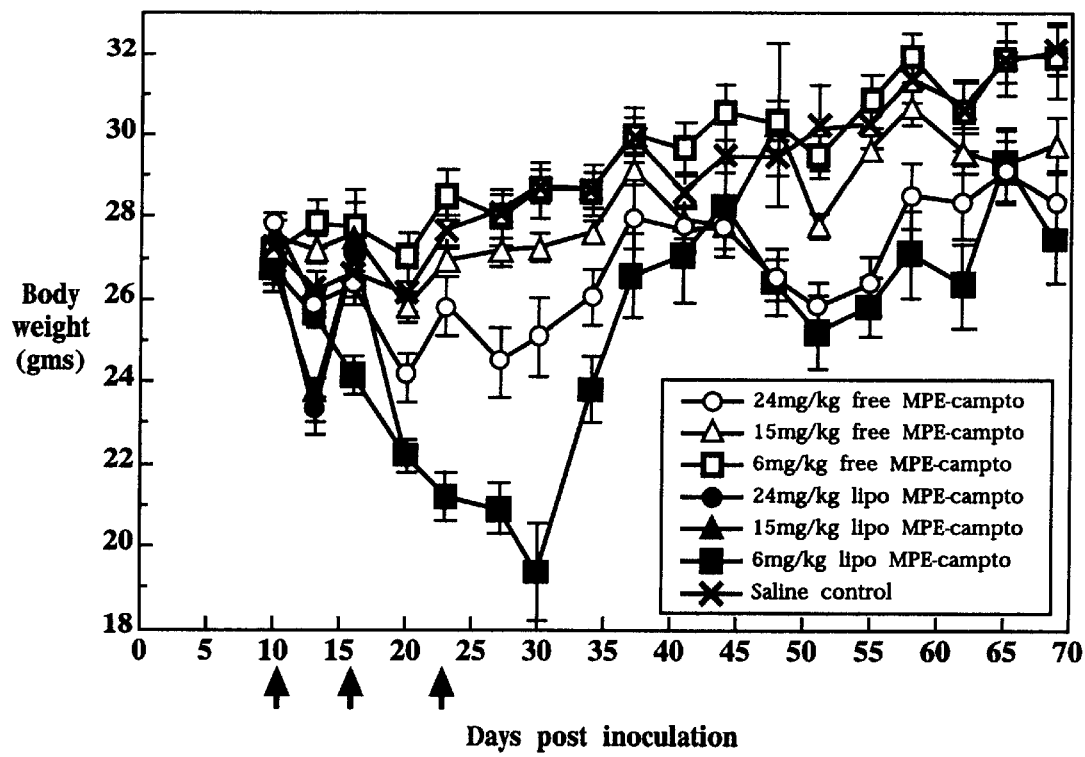
FIG. 2A is a plot showing the body weight of mice, in grams, as a function of days after tumor inoculation with an HT29 colon tumor. The animals were treated on days 10, 16 and 23 after tumor inoculation with liposome-entrapped MPE-camptothecin at dosages of 24 mg/kg (closed circles), 15 mg/kg (closed triangles) and 6 mg/kg (closed squares) and with free MPE-camptothecin at doses of 24 mg/kg (open circles), 15 mg/kg (open triangles) and 6 mg/kg (open squares)
Figure 2B:
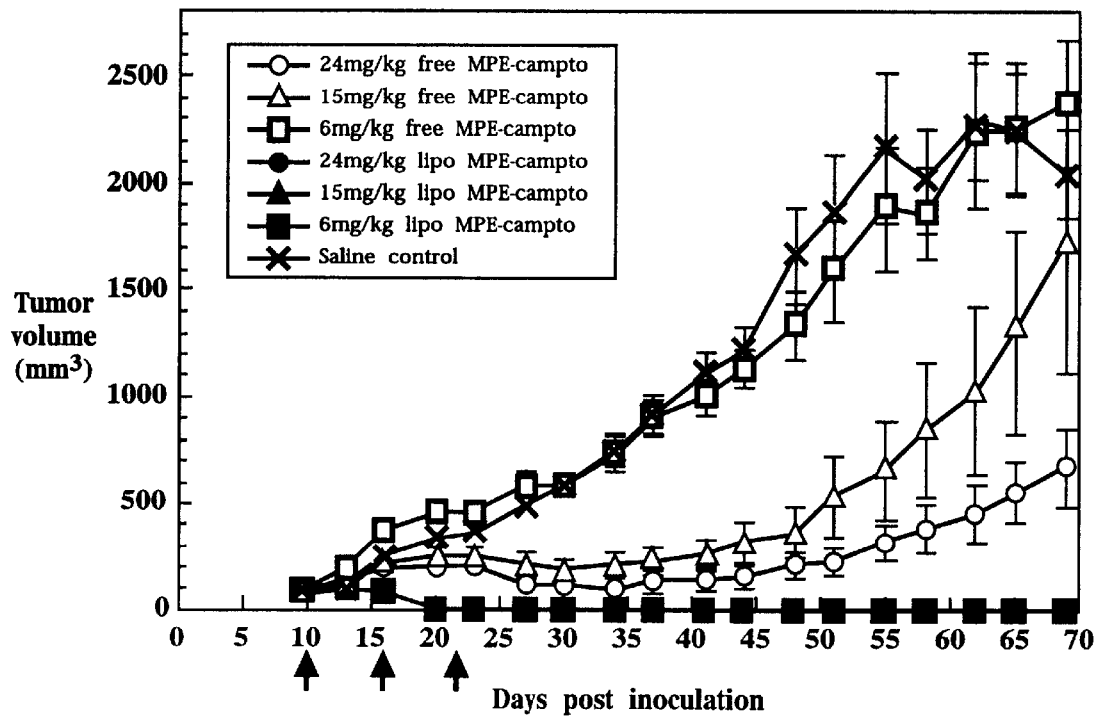
FIG. 2B is a plot showing tumor volume, in $mm^3$, as a function of days after inoculation with an HT29 colon tumor. The animals were treated on days 10, 16 and 23 after tumor inoculation with liposome-entrapped MPE-camptothecin at dosages of 24 mg/kg (closed circles), 15 mg/kg (closed triangles) and 6 mg/kg (closed squares) and with free drug at doses of 24 mg/kg (open circles), 15 mg/kg (open triangles) and 6 mg/kg (open squares)

The body weight of each test animal and the tumor volume of each animal are shown, respectively in FIGS. 2A and 2B, where animals were treated with liposomal entrapped MPE-camptothecin at dosages of 24 mg/kg (closed circles), 15 mg/kg (closed triangles) and 6 mg/kg (closed squares) and with free MPE-camptothecin at doses of 24 mg/kg (open circles), 15 mg/kg (open triangles) and 6 mg/kg (open squares).

With respect to the animals treated with the liposome-entrapped MPE-camptothecin, all of the animals dosed with 15 mg/kg and 24 mg/kg died after two doses due to drug-related toxicity, with most deaths on day five after the first dose. All 10 of the animals treated with 6 mg/kg liposome-entrapped MPE-camptothecin survived until administration of the third dose on day 23, after which five of the ten animals died within a few days. The toxicity of the liposome-entrapped MPE-camptothecin is reflected in the greater body weight losses, as seen in FIG. 2A.

In contrast, all of the animals treated with the free form of the drug survived the study, with the exception of one animal in the 24 mg/kg dosing group that died a few days after the third dose on day 23.

TABLE 1

| Treatment | Dose mg/kg | Number of Test Animals | Number of Surviving Animals | | |
|---|---|---|---|---|---|
| | | | after dose 1 (day 9) | after dose 2 (day 16) | after dose 3 (day 23) |
| Saline | na | 20 | 20 | 20 | 20 |
| free MPE-camptothecin | 24 | 10 | 10 | 10 | 9 |
| free MPE-camptothecin | 15 | 10 | 10 | 10 | 10 |
| free MPE-camptothecin | 6 | 10 | 10 | 10 | 10 |
| liposome-entrapped | 24 | 10 | 1 | 0 | 0 |
| liposome-entrapped | 15 | 10 | 5 | 0 | 0 |
| liposome-entrapped | 6 | 10 | 10 | 10 | 5 |

With respect to antitumor activity of the formulations, the liposome-entrapped MPE-camptothecin was more effective than the free form of the drug in inhibiting tumor growth, despite its greater toxicity. This can be seen in FIG. 2B, where the 6 mg/kg dose of liposome-entrapped MPE-camptothecin was significantly more effective in inhibiting tumor growth (log growth rate of −0.026) than even the highest dose level of free MPE-camptothecin (24 mg/kg, log growth rate 0.0048).

The complete and partial remission of the tumors in the test animals was monitored and is presented in Table 2. Complete remission of a tumor is defined as the elimination of tumor mass until the end of the experiment. A partial remission is defined as a tumor volume of less than 50% of the peak tumor volume for an individual animal.

TABLE 2

| Treatment | Dose mg/kg | Complete Remission[1] | Partial Remission[2] |
|---|---|---|---|
| Saline | | 0/20 | 0/20 |
| free MPE-camptothecin | 24 | 3/10 | 1/10 |
| free MPE-camptothecin | 15 | 2/10 | 0/10 |
| free MPE-camptothecin | 6 | 0/10 | 0/10 |
| liposome-entrapped | 24 | —[3] | —[3] |
| liposome-entrapped | 15 | —[3] | —[3] |
| liposome-entrapped | 6 | 10/10 | na[4] |

[1]complete remission defined as elimination of tumor mass until experiment termination.
[2]partial remission defined as a tumor volume of less than 50% of the peak tumor volume for an individual animal.
[3]all 10 animals in test groups died after the second dose on day 16.
[4]na = not applicable As can be seen in Table 2, the liposome-entrapped MPE-camptothecin at a dose of 6 mg/kg was effective to cause a complete remission of tumors in all 10 test animals. This effect was observed within five days after the second treatment on day 16. As noted above, five of the test animals in the 6 mg/kg liposome-entrapped test group died shortly after the third dose. In the surviving five animals, the tumors did not recur by the end of the study, approximately 30 days after the final treatment on day 23. Data is unavailable for the animals treated with 15 mg/kg and 24 mg/kg liposome-entrapped MPE-camptothecin, since all of the animals in these test groups died due to drug-related toxicity, as noted above.

Administration of MPE-camptothecin in free form at a dose of 24 mg/kg resulted in 3 animals with complete tumor remission and 1 animal with partial tumor remission, as seen in Table 2.

Comparison of the results observed for the drug administered in free form and in liposome-entrapped form indicate that the drug is more potent when administered in liposome-entrapped form. In fact, the liposome-entrapped drug is at least four times more potent than the free form of the drug, as can be seen by comparing the results obtained for a 6 mg/kg of liposome-entrapped MPE-camptothecin dosage to a 24 mg/kg free MPE-camptothecin dosage (FIG. 2B, Table 2). It is clear from these results that the dose of liposome-entrapped MPE-camptothecin required for therapeutically effective anti-tumor therapy is four times lower than the dose required when the drug is administered in free form.

Example 2 describes the details of a second study to determine the maximum tolerated dose and the lowest effective dose of the liposome-entrapped MPE-camptothecin. In this study, liposomes were prepared as described in Example 1 and the liposome formulation was administered to test animals at drug dosages of 0.1 mg/kg, 0.5 mg/kg, 1 mg/kg, 3 mg/kg and 5 mg/kg. The free drug was administered at 20 mg/kg as a comparison.

Table 3 summarizes the number of test animals in each group, specifying the number of animals surviving at each dosing phase of the study. As seen in the table, all of the control, saline treated animals and all of the animals treated with free MPE-camptothecin survived for the duration of the study. Of the ten animals treated with 5 mg/kg liposome-entrapped MPE-camptothecin, four of the animals died of drug-related toxicity and one additional animal died of apparently nonspecific causes after the third dose. One of the ten animals in the test group receiving 3 mg/kg liposome-entrapped MPE-camptothecin died after the second dose, but the death was not considered due to drug treatment because of the absence of any correlating signs of toxicity. All other animals treated with liposome-entrapped MPE-camptothecin survived the entire study duration.

TABLE 3

| Treatment | Dose mg/kg | Number of Test Animals | Number of Surviving Animals | | |
|---|---|---|---|---|---|
| | | | after dose 1 (day 9) | after dose 2 (day 16) | after dose 3 (day 23) |
| Saline | | 20 | 20 | 20 | 20 |
| free MPE-camptothecin | 20 | 10 | 10 | 10 | 10 |
| liposome-entrapped | 5 | 10 | 10 | 10 | 5 |
| liposome-entrapped | 3 | 10 | 10 | 9 | 9 |
| liposome-entrapped | 1 | 10 | 10 | 10 | 10 |
| liposome-entrapped | 0.5 | 10 | 10 | 10 | 10 |
| liposome-entrapped | 0.1 | 10 | 10 | 10 | 10 |

Figure 3A:
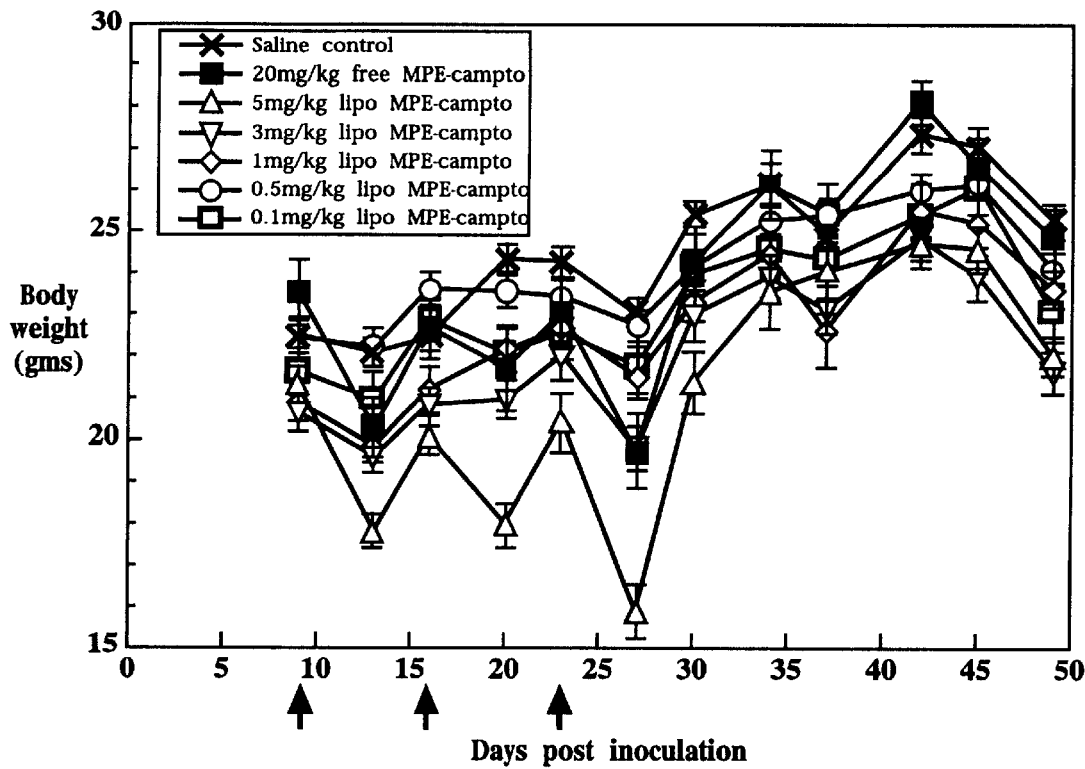
FIG. 3A is a plot showing the body weight of mice, in grams, as a function of days after inoculation with an HT29 colon tumor. The animals were treated on days 9, 16 and 23 after tumor inoculation with liposome-entrapped MPE-camptothecin at dosages of 5 mg/kg (open triangles), 3 mg/kg (open inverted triangles), 1 mg/kg (open diamonds), 0.5 mg/kg (open circles) and 0.1 mg/kg (open squares) and with free MPE-camptothecin at a dose of 20 mg/kg (closed squares)
Figure 3B:
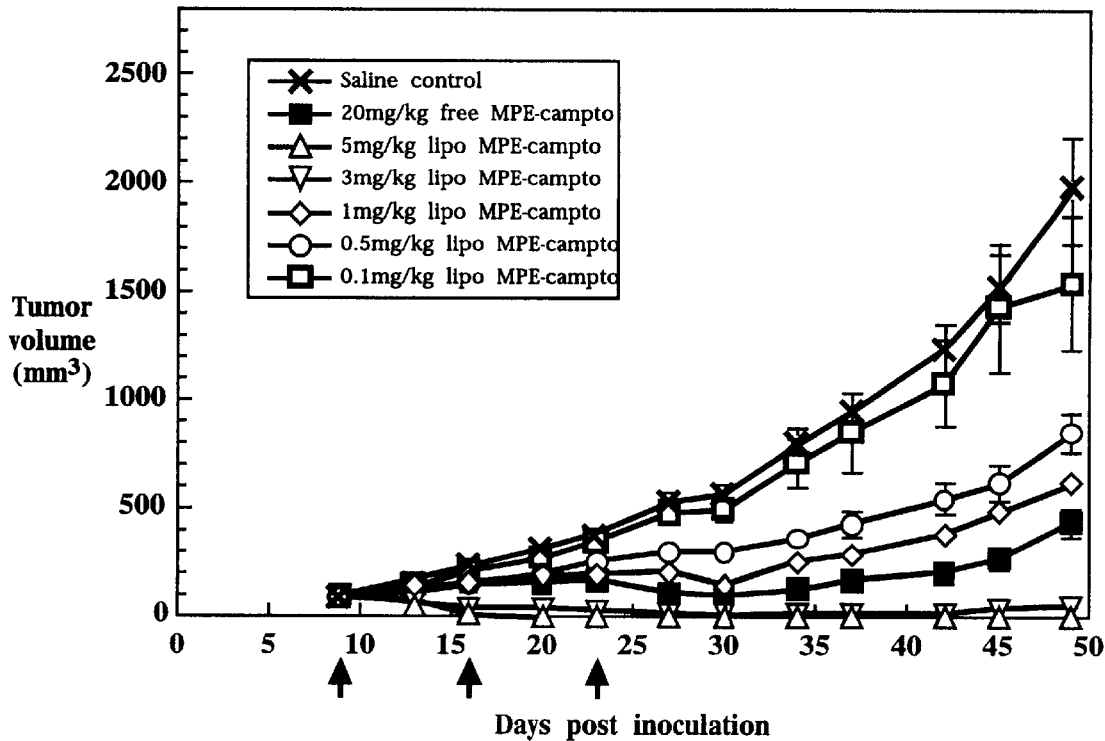
FIG. 3B is a plot showing tumor volume, in $mm^3$, as a function of days after inoculation with an HT29 colon tumor. The animals were treated on days 9, 16 and 23 after tumor inoculation with liposome-entrapped MPE-camptothecin at dosages of 5 mg/kg (open triangles), 3 mg/kg (open inverted triangles), 1 mg/kg (open diamonds), 0.5 mg/kg (open circles) and 0.1 mg/kg (open squares) and with free MPE-camptothecin at a dose of 20 mg/kg (closed squares)

The results of the study are shown in FIGS. 3A–3B, where FIG. 3A shows the body weight of mice, in grams, as a function of days after inoculation with the HT-29 colon tumor. The animals were treated on days 9, 16 and 23 after tumor inoculation with liposomal entrapped topoisomerase I inhibitor at dosages of 5 mg/kg (open triangles), 3 mg/kg (open inverted triangles), 1 mg/kg (open diamonds), 0.5 mg/kg (open circles) and 0.1 mg/kg (open squares) and with free drug at a dose of 20 mg/kg (closed squares). As can be seen in FIG. 3A, body weight changes were dose-related and, these changes were correlated with other observations of toxicity.

FIG. 3B is a similar plot showing tumor volume, in mm$^3$, as a function of days after tumor inoculation, where the dosages are represented by the same symbols as in FIG. 3A. FIG. 3B shows that both the 5 mg/kg and 3 mg/kg dose levels of liposome-entrapped MPE-camptothecin were more therapeutically effective in inhibiting tumor growth than the 20 mg/kg dose of the free drug. Treatment with 20 mg/kg of free MPE-camptothecin (log growth rate of 0.011) was approximately equivalent in antitumor activity to the 1 mg/kg dosage level of the drug in liposome-entrapped form (log growth rate of 0.017).

Table 4 summarizes the complete and partial tumor remission in the test animals.

TABLE 4

| Treatment | Dose mg/kg | Complete Remission[1] | Partial Remission[2] |
|---|---|---|---|
| Saline | | 0/20 | 0/20 |
| free MPE-camptothecin | 20 | 0/10 | 1/10 |
| liposome-entrapped MPE-camptothecin | 5 | 10/10 | na[3] |
| liposome-entrapped MPE-camptothecin | 3 | 7/10 | 1/10 |
| liposome-entrapped MPE-camptothecin | 1 | 0/10 | 0/10 |
| liposome-entrapped MPE-camptothecin | 0.5 | 0/10 | 1/10 |
| liposome-entrapped MPE-camptothecin | 0.1 | 0/10 | 0/10 |

[1]Complete remission defined as elimination of tumor mass until experiment termination.
[2]Partial remission defined as a tumor volume of less than 50% of the peak tumor volume for an individual animal.
[3]na = not applicable There were no complete tumor remissions in the animals treated with 20 mg/kg of free MPE-camptothecin. In contrast, all ten of the animals treated with liposome-entrapped MPE-camptothecin at the 5 mg/kg dosage level had complete remissions. At the 3 mg/kg dosage, seven of the animals had complete remission of their tumor.

The results from the study of Example 3 shows that antitumor activity of the liposome-entrapped topoisomerase inhibitor MPE-camptothecin is significantly better when compared to the free form of the drug, indicating that the liposome-entrapped form was about 20-fold more potent since the antitumor activity of the free drug at a dose of 20 mg/kg was most comparable to the activity of a 1 mg/kg dose of the liposome-entrapped form of the drug. That the 3 mg/kg and 5 mg/kg liposome-entrapped MPE-camptothecin dosages were significantly more effective in antitumor therapy than the 20 mg/kg dose of the drug in free form indicates that the therapeutic index of the drug entrapped in liposomes is approximately four-fold to five-fold higher than the drug in free form.

2. In Vivo Administration of Topotecan

In another study performed in support of the invention, topotecan was entrapped in liposomes composed of DSPC and mPEG-DSPE in a 95:5 molar ratio, as described in Example 4. Early studies, not reported here, indicated that topotecan was not readily retained in the liposomes. The lipid bilayer was selected to use a single component phospholipid having an acyl chain length close to DSPE in the mPEG-DSPE component. Such a bilayer has minimal packing defects which arise from imperfections in nearest neighbor interactions in a solid phase bilayer, which have reduced lateral and rotational mobility relative to fluid bilayers. In addition, a dextran-sulfate loading battery was used in order to achieve precipitation of the topotecan in the liposome interior. Other polymers, in particular polyanionic polymers, are suitable for this purpose, such as chondroitin sulfate A, polyvinylsulfuric acid, and polyphosphoric acid.

The pre-formed liposomes containing dextran ammonium sulfate in the central compartment were loaded with topotecan as described in Example 4. After loading, unentrapped drug was removed by diafiltration and the liposomes were characterized. The liposomes were loaded to a drug:lipid ratio of 0.238 and the liposomes had an average particle diameter of 87 nm.

Figure 4A:
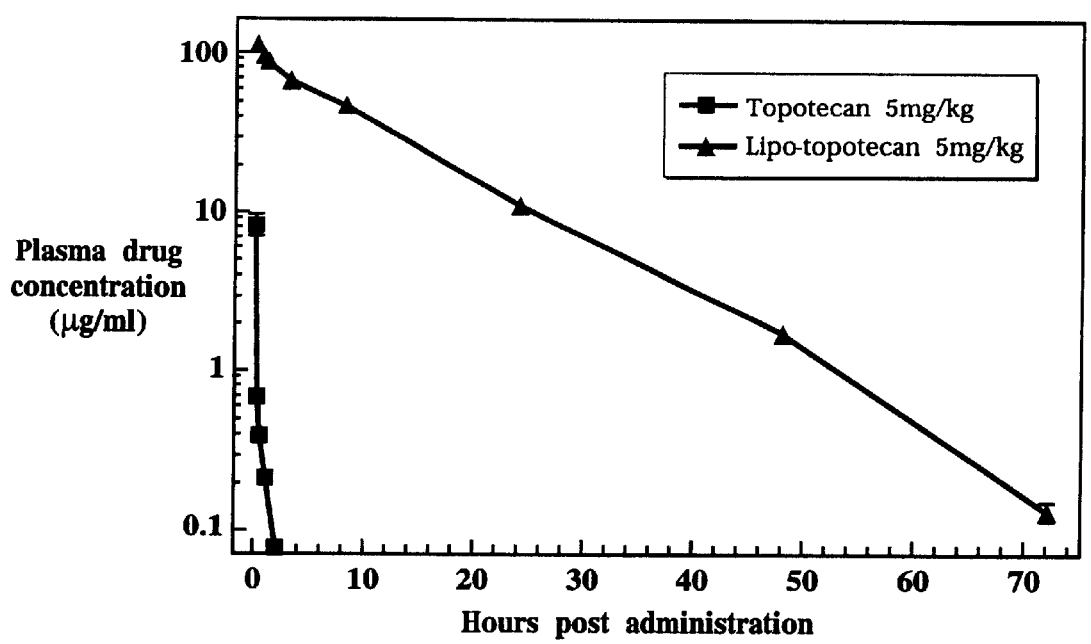
FIGS. 4A–4B are plots showing the plasma concentration of topotecan as a function of time, in hours, after administration of liposome-entrapped topotecan (solid triangles) and of free (non-liposomal) topotecan (solid squares) to rats at dosages of 2 mg/kg (FIG. 4A) and 5 mg/kg (FIG. 4B)
Figure 4B:
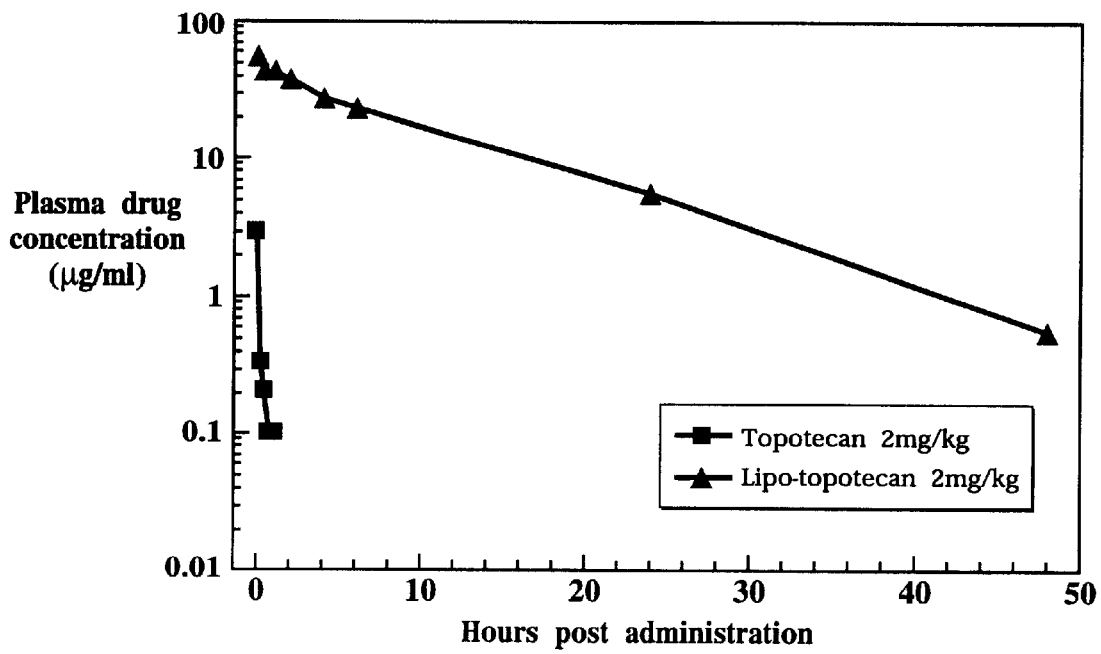

The liposomes containing topotecan were administered intraveneously to rats to determine the blood circulation lifetime. FIGS. 4A–4B show the plasma concentration of topotecan as a function of time after administration to rats. FIG. 4A compares the concentration of liposome-entrapped topotecan administered at 2 mg/kg (solid triangles) to the concentration of free topotecan administered at the same dosage (solid squares). FIG. 4B compares the two forms of the drug at a dosage of 5 mg/kg. The calculated pharmacokinetic parameters are given in Table 5.

TABLE 5

| Parameter | Dosage = 2 mg/kg | | Dosage = 5 mg/kg | |
|---|---|---|---|---|
| | Free Topotecan | Liposome Entrapped | Free Topotecan | Liposome Entrapped |
| lasma Cmax ($\mu$g/mL) | 2.89 | 54.5 | 8.23 | 119.3 |
| AUC ($\mu$g/mL h) | 0.57 | 523 | 1.57 | 1140 |
| T ½ (h) | 0.20 | 7.2 | 0.30 | 9.8 |
| CL (mL/h) | 887 | 0.96 | 820 | 1.10 |
| Vol. Dist. (mL) | 173 | 9.2 | 278 | 17.5 |
| elimination rate constant (l/h) | 3.45 | 0.096 | 2.33 | 0.071 |

The data in Table 5 shows that the liposome-entrapped drug has a significantly longer circulation time than the free form of the drug.

The efficacy of the liposomes was determined in another study. As described in Example 4, the liposomes were administered to mice bearing a subcutaneous xenograft tumor. Tumor-bearing mice were randomized into six treatment groups of 12 mice for treatment with one of the following: saline, liposome-entrapped MPE-camptothecin 4 mg/kg; free topotecan 25 mg/kg; liposome entrapped topotecan at drug dosages of 2 mg/kg, 5 mg/kg or 8 mg/kg. All treatments were administered as intravenous bolus injections given weekly for 3 treatments, specifically on days 9, 16 and 23.

The tumor size in each animal was measured twice weekly during the study to evaluate therapeutic efficacy. Body weight of each animal was monitored twice weekly to assess toxicity of the formulations. The results are shown in Tables 6 and 7 and in FIGS. 5A–5B.

TABLE 6

| Treatment | Dose mg/kg | Complete Re-mission[1] | Partial Re-mission[2] | Non-Responsive[3] |
|---|---|---|---|---|
| Saline | | 0 | 0 | 12 |
| liposome-entrapped MPE-camptothecin | 4 | 8 | 4 | 0 |
| free topotecan | 25 | 0 | 1 | 11 |
| liposome-entrapped topotecan | 2 | 1 | 2 | 9 |
| liposome-entrapped topotecan | 5 | 2 | 8 | 2 |
| liposome-entrapped topotecan | 8 | 7 | 3 | 2 |

[1]Complete remission defined as elimination of tumor mass until experiment termination.
[2]Partial remission defined as a tumor volume of less than 50% of the peak tumor volume for an individual animal.
[3]Non-responsive defined as a tumor volume equal to or greater than initial tumor volume.

Figure 5A:
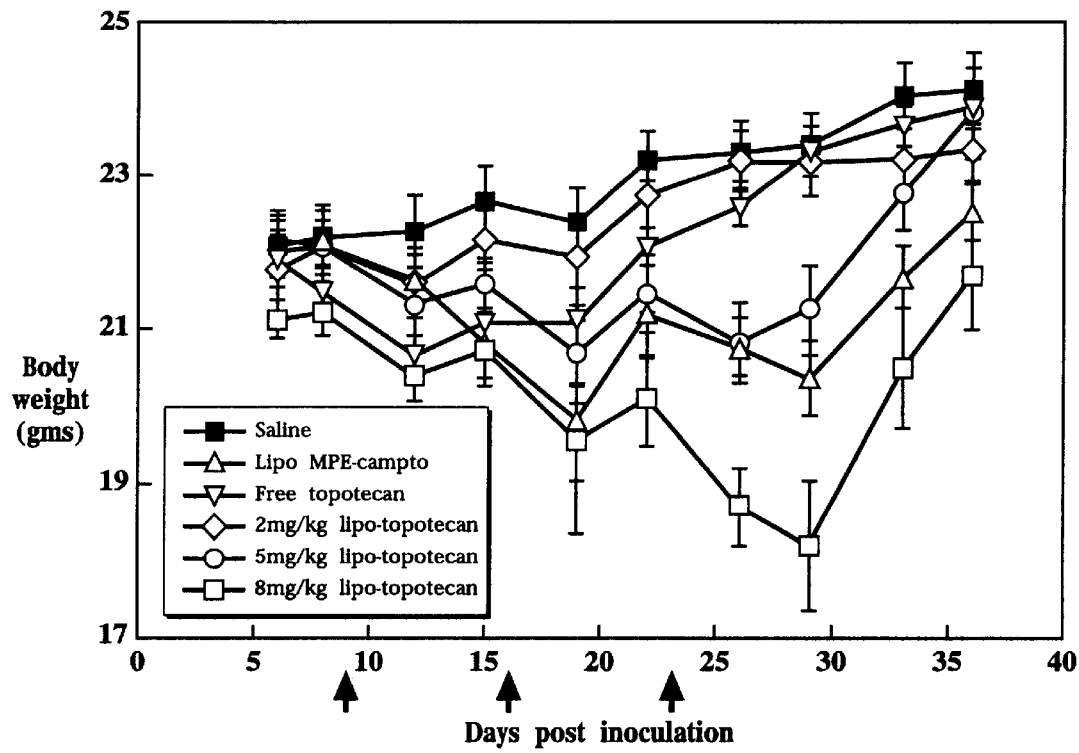
FIG. 5A is a plot showing the body weight of mice, in grams, as a function of days after inoculation with an HT29 colon tumor. The animals were treated on days 9, 16 and 23 after tumor inoculation with liposome-entrapped topotecan at dosages of 2 mg/kg (diamonds), 5 mg/kg (circles), 8 mg/kg (open squares); liposome-entrapped MPE-camptothecin at 4 mg/kg (triangles); free topotecan at a dose of 25 mg/kg (inverted triangles) and saline (closed squares)

As can be seen from FIGS. 5A and Table 6, left untreated the tumors grew at a rate of 17.8 mm³ per day for the duration of the study. The animals treated with liposome-entrapped MPE-camptothecin (positive control animals) experienced a tumor growth rate –1.2 mm³ per day for the duration of the study. Animals treated with nonencapsulated topotecan, which was administered at 25 mg/kg somewhat below the maximum tolerated dosage (MTD) of 40 mg/kg, had tumor growth of 14.1 mm³ per day. Animals treated with liposome-entrapped topotecan had tumor growth of 0.9 mm³ per day for a dosage of 2 mg/kg, –1.9 mm³ per day for a dosage of 5 mg/kg and –0.8 mm³ per day for a dosage of 8 mg/kg. The negative growth rate indicates regression of tumor size below the starting tumor volume.

The size of treated tumors as a function of the size of control tumors (%T/C) was examined for all treatment groups and is summarized in Table 6. The National Cancer Institute defines significant anti-tumor activity as a %T/C less than 42.

TABLE 7

| Treatment | Dose mg/kg | % T/C[1] Day 29 | % T/C Day 33 | % T/C Day 36 |
|---|---|---|---|---|
| liposome-entrapped MPE-camptothecin | 4 | 1.8 | 0.6 | 1.9 |
| free topotecan | 25 | 82.8 | 79.0 | 85.9 |
| liposome-entrapped topotecan | 2 | 19.5 | 12.9 | 16.3 |
| liposome-entrapped topotecan | 5 | 10.5 | 5.6 | 5.6 |
| liposome-entrapped topotecan | 8 | 2.0 | 2.2 | 2.2 |

[1]% T/C defined as the average tumor volume at day indicated over the average tumor volume of the control, saline treated animals.

3. In Vivo Administration of CKD-602

Example 5 describes another study conducted in support of the invention using the topoisomerase inhibitor CKD-602. The drug was remotely loaded into liposomes against an ammonium-sulfate gradient with dextran as a trapping agent. The liposome lipid composition was identical to that used for the study using topotecan-HSPC and mPEG-DSPE in a 95/5 mole ratio.

Figure 6:
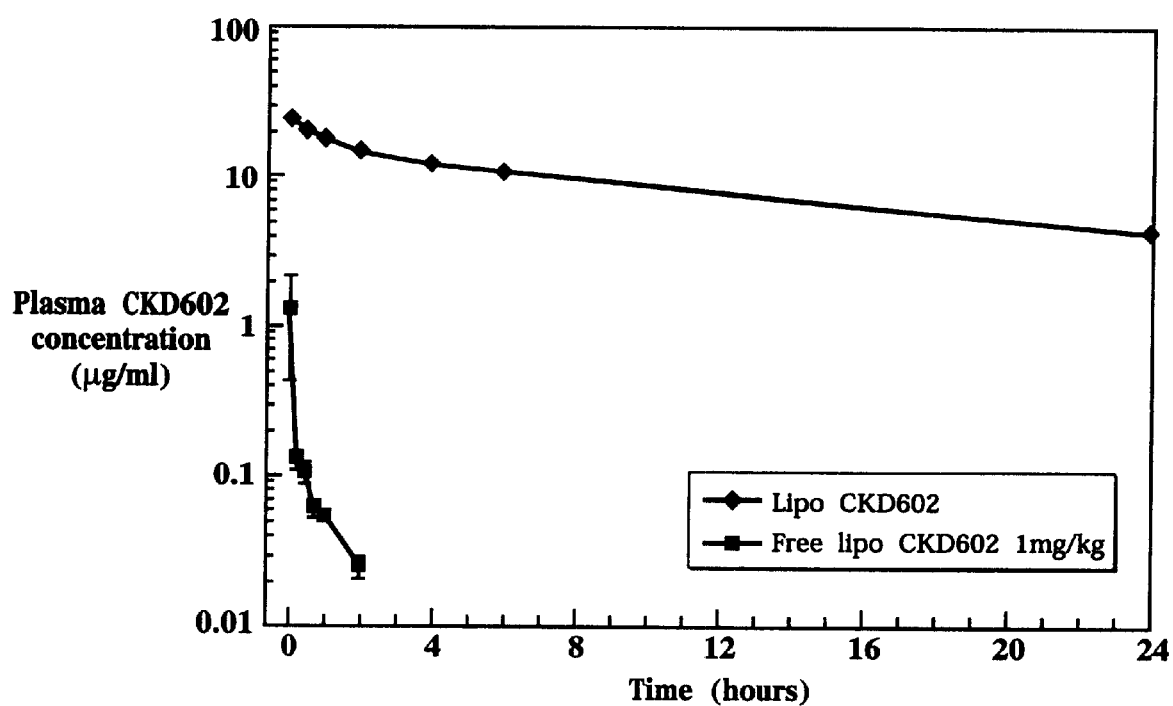
FIG. 6 is a plot of plasma concentration of CKD602 as a function of time, in hours, after administration of liposome-entrapped CKD602 (solid circles) and of free (non-liposomal) topotecan (solid squares) to rats at a dosage of 1 mg/kg.

FIG. 6 is a plot showing the plasma concentration of CKD-602 as a function of time after administration to rats at a dosage of 1 mg/kg. The liposome-entrapped form of the drug (solid circles) had a calculated half-life of 9.8 hours and an AUC of 274 $\mu$g/mL/hr. The free form of the drug had a calculated half-life of 0.2 hours and an AUC of 0.37 $\mu$g/mL/hr.

Therapeutic efficacy of the CKD-602 formulation was evaualted using mice bearing a HT-29 colon cancer xenograft. Seventy-two mice were inoculated with HT-29 tumor cells and nine days later were randomized into six treatment groups. The animals in each group were treated with one of the following formulations: saline, liposome-entrapped MPE-camptothecin 4 mg/kg; free CKD-602 20 mg/kg; liposome entrapped CKD-602 at drug dosages of 1 mg/kg, 2 mg/kg or 4 mg/kg. All treatments were administered as intravenous bolus injections given weekly for 3 treatments, specifically on days 11, 18 and 25.

Figure 7A:
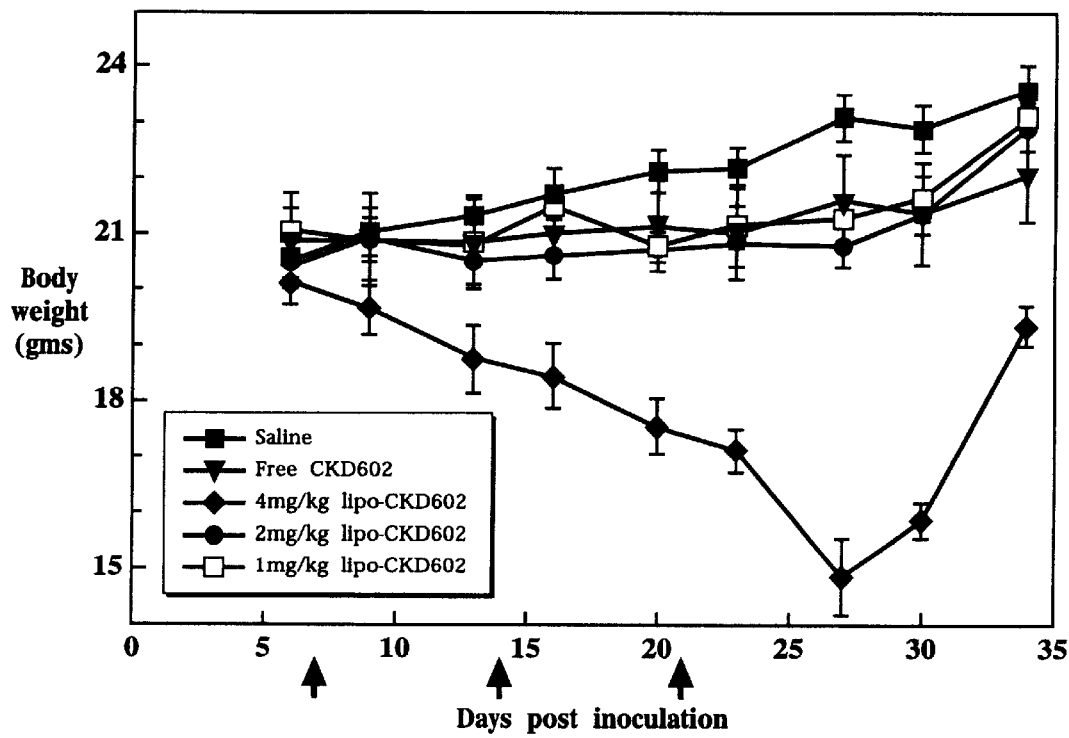
FIG. 7A is a plot showing the body weight of mice, in grams, as a function of days after inoculation with an HT29 colon tumor. The animals were treated on days 9, 16 and 23 after tumor inoculation with liposome-entrapped CKD602 at dosages of 4 mg/kg (diamonds), 2 mg/kg (circles), 1 mg/kg (open squares); liposome-entrapped MPE-camptothecin at 4 mg/kg (triangles); free CKD602 at a dose of 20 mg/kg (inverted triangles) and saline (closed squares)

The tumor size in each animal was measured twice weekly during the study to evaluate therapeutic efficacy. Body weight of each animal was monitored twice weekly to assess toxicity of the formulations. The results are shown in Tables 8 and 9 and in FIGS. 7A–7B.

TABLE 8

| Treatment | Dose mg/kg | Complete Re-mission[1] | Partial Re-mission[2] | Non-Responsive[3] |
|---|---|---|---|---|
| Saline | | 0/10 | 0/10 | 10/10 |
| liposome-entrapped MPE-camptothecin | 4 | 6/10 | 0/10 | 4/10 |

TABLE 8-continued

| Treatment | Dose mg/kg | Complete Remission[1] | Partial Remission[2] | Non-Responsive[3] |
|---|---|---|---|---|
| free CKD602 | 20 | 0/6 | 0/6 | 6/6 |
| liposome-entrapped CKD602 | 1 | 2/10 | 7/10 | 1/10 |
| liposome-entrapped CKD602 | 2 | 6/10 | 2/10 | 2/10 |
| liposome-entrapped CKD602 | 4 | 4/4 | 0/4 | 0/4 |

[1]Complete remission defined as elimination of tumor mass until experiment termination.
[2]Partial remission defined as a tumor volume of less than 50% of the peak tumor volume for an individual animal.
[3]Non-responsive defined as a tumor volume equal to or greater than initial tumor volume.

Figure 7B:
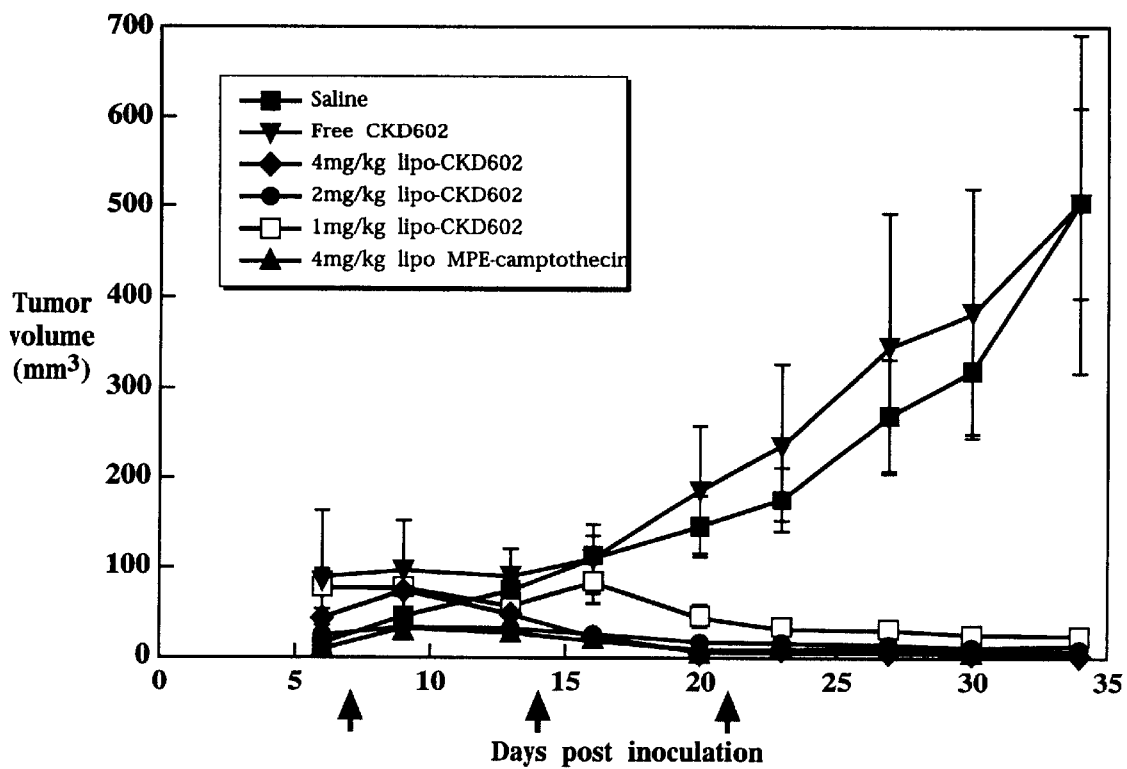
FIG. 7B is a plot showing tumor volume, in mm$^3$, as a function of days after inoculation with an HT29 colon tumor. The animals were treated on days 9, 16 and 23 after tumor inoculation with liposome-entrapped CKD602 at dosages of 4 mg/kg (diamonds), 2 mg/kg (circles), 1 mg/kg (open squares); liposome-entrapped MPE-camptothecin at 4 mg/kg (triangles); free CKD602 at a dose of 20 mg/kg (inverted triangles) and saline (closed squares).

As can be seen in Table 8 and in FIG. 7B, the animals treated with saline experienced continuous tumor growth, at a rate of 15.45 mm$^3$ per day for the duration of the study. The animals treated with the liposome-entrapped MPE-camptothecin (positive control animals) had a tumor growth rate of −0.63 mm$^3$ per day for the duration of the study. Animals treated with free, unentrapped CKD602 had tumor growth of 15.21 mm$^3$ per day. Animals treated with liposomal CKD602 had tumor growth of −2.21 mm$^3$ per day for animals treated with a dose of 1 mg/kg, −0.96 mm$^3$ per day for a dose of 2 mg/kg and −2.37 mm$^3$ per day for a dose of 4 mg/kg. The negative growth rate indicates regression of tumor size below the starting tumor volume.

The size of treated tumors as a function of the size of control tumors (%T/C) was examined for all treatment groups and is summarized in Table 9. The National Cancer Institute defines significant anti-tumor activity as a %T/C less than 42.

TABLE 9

| Treatment | Dose mg/kg | % T/C[1] Day 29 | % T/C Day 33 | % T/C Day 36 |
|---|---|---|---|---|
| liposome-entrapped MPE-camptothecin | 4 | 2.9 | 2.3 | 1.6 |
| free CKD602 | 20 | 129.1 | 120.1 | 99.9 |
| liposome-entrapped CKD602 | 1 | 11.4 | 7.7 | 4.4 |
| liposome-entrapped CKD602 | 2 | 4.8 | 2.8 | 1.6 |
| liposome-entrapped CKD602 | 4 | 1.0 | 1.3 | 0.9 |

[1]% T/C defined as the average tumor volume at day indicated over the average tumor volume of the control, saline treated animals.

IV. EXAMPLES

The following examples illustrate methods of preparing, characterizing, and using the composition of the present invention. The examples are in no way intended to limit the scope of the invention.

Materials

The topoisomerase inhibitor (7-(4-methyl-piperazinomethylene)-10,11-ethylenedioxy-20(S)-camptothecin trifluoroacetate (GI147211) (MPE-camptothecin), was provided by Glaxo Research Institute, Research Triangle Park, N.C. CKD602 (7-(2-(N-isopropylamino)ethyl)-(20S)-camptothecin) was provided by Chong Kun Dang Corporation, Seoul Korea. Topotecan (Hycamtin®) was purchased commercially.

Materials for preparation of the liposomes and all other reagents were from commercially available sources.

Methods

Animal Studies: Homozygous nude mice were obtained from Taconic Farms (Germantown, N.Y.) and allowed to acclimate for 7 days prior to initiation of the experiment. Animals were housed in appropriate isolated caging with ad lib sterile rodent food and acidified water and a 12:12 light:dark cycle. Animals were randomized into treatment groups prior to tumor inoculation based on body weight. Randomization was confirmed based on tumor size immediately prior to initiation of treatment.

Tumors: Tumors were inoculated by trochar placement of fragments from rapidly growing tumors on donor animals. The human colon cancer cell line, HT-29, was used to initiate subcutaneous xenograft tumors. Cultured cells were trypsinized, washed, counted and resuspended at 50 million cells per mL normal growth media. Tumors were inoculated by injection of 0.1 mL (5 million cells) at the back of the neck. Tumors were allowed to grow to an average size of 100 mm$^3$ prior to initiation of treatment.

Monitoring: All animals were observed daily for general well-being throughout the experiments. Animals were weighed prior to tumor inoculation and weekly thereafter. Tumors were measured twice weekly throughout the experiment, beginning 5–10 days after tumor inoculation. Any animal observed to have 15% or greater weight loss from the initial starting weight and any animal observed to have greater than 4,000 mm$^3$ tumor volume were excluded from the study.

Example 1

Preparation of Liposomes with Entrapped Topoisomerase Inhibitor

Liposomes were prepared and loaded with a selected topoisomerase inhibitor as follows.

A. Liposome Preparation

The lipids hydrogenated soy phosphaticylcholine (HSPC), cholesterol (Chol) and mPEG-DSPE (at a ratio of 56.4:38.3:5.3 mol/mol) were dissolved in ethanol at 65° C. in a 250 mL round bottom. The lipids were agitated continuously for at least 30 minutes at 65° C. The total lipid concentration in ethanol solution was 3.7 g total lipid per 10 mL ethanol.

The dissolved lipid solution was transferred to another 250 mL round bottom flask containing 100 mL of 250 mM ammonium sulfate solution equilibrated to 65° C. The ethanol:lipid:ammonium sulfate hydration mixture was mixed continuously for at least one hour while maintaining the temperature using a 65° C. water bath to form oligolamellar ethanol hydration liposomes.

The oligolamellar liposomes were size reduced using a Lipex thermobarrel extruder to pass the hydration mixture through polycarbonate membranes with known pore size dimensions. The mixture was passed 5 times through a 0.20 μm pore diameter membrane, followed by 10 passes through a 0.10 μm pore diameter membrane. The extruded liposomes contained ammonium sulfate within the interior aqueous compartment(s) of the liposomes, as well as in the exterior aqueous bulk phase medium in which they are suspended. The sized liposomes were stored in the refrigerator until diafiltration preceding the remote loading procedure.

100 mg of a selected topoisomerase inhibitor, MPE-camptothecin, CKD-602 or topotecan, was dissolved in 40 mL 10% sucrose solution to yield a concentration of 2.5 mg/mL. After dissolution, the solution was passed through a 0.20 μm filter to remove insoluble particulates.

B. Remote Loading of Liposomes

Ammonium sulfate and ethanol were removed from the external bulk aqueous phase immediately prior to remote loading by hollow fiber tangential flow diafiltration with a 100 KDa nominal molecular weight cutoff cartridge. Constant feed volume was maintained, and at least seven exchange volumes were used resulting in liposomes suspended in an exterior aqueous phase comprised of 10% sucrose.

After diafiltration, the liposomes were mixed with a selected drug solution at a ratio (drug solution:liposomes) of 1:4 (vol/vol) and rapidly warmed to 65° C. using a pre-equilibrated jacketed vessel containing water. The temperature of the mixture was maintained at 65° C. for 40 to 60 minutes, after which the mixture was rapidly cooled in an ice-water bath. After remote loading, a sample of the liposomes was taken to check for the presence of crystals, to determine percent encapsulation and to measure the mean particle diameter.

Unencapsulated drug was removed from the bulk phase medium by hollow fiber tangential flow diafiltration using a 100 kDa nominal molecular weight cutoff cartridge. At least eight exchange volumes were used, resulting in liposomally encapsulated drug suspended in an external aqueous phase comprised of 10% sucrose 10 millimolar Histidine pH 6.5.

The final liposome preparation was sterile filtered using a 0.22 µm cellulose acetate syringe filter and stored refrigerated and protected from light until use.

C. Characterization of Liposomes

Percent encapsulation was determined using size exclusion chromatography to compare the percent drug in the void volume (liposomal encapsulated) to the total drug (void volume plus included volume). Drug concentration in the column fractions was determined by absorbance. Mean particle diameter was determined using quasielectric laser light scattering (QELS). The total lipid concentration was assayed at the post-sterile filtration stage in order to determine the drug to lipid ratio. Liposomes loaded with MPE-camptothecin, topotecan and 7-(2-(N-isopropylamino) ethyl)-(20S)-camptothecin (CKD-602) were prepared and characterized. The results are shown in the table below.

| Parameter | liposome-entrapped MPE-camptothecin | liposome-entrapped Topotecan | liposome-entrapped CKD-602 |
| --- | --- | --- | --- |
| lot no. | 221AZ43A | 221AZ43B | 221AZ53 |
| Total Lipid concentration | 17.81 µmol/mL | 15.97 µmol/mL | 14.079 µmol/mL |
| Drug concentration | 2.69 mg/mL (4.55 µmol/mL) | 1.72 mg/mL (3.76 µmol/mL) | 1.77 mg/mL (3.77 µmol/mL) |
| drug:lipid ratio (mol/mol) | 0.26 (1:3.92) | 0.24 (1:4.25) | 0.27 (1:3.73) |
| Mean Particle diameter | 99 nm | 95.4 nm | 96.7 nm |
| Percent Encapsulation | 96.4% | 99.9% | 95.3% |

Example 2

In Vivo Efficacy of Liposome-entrapped MPE-Camptothecin

Liposomes containing entrapped MPE-camptothecin were prepared as described in Example 1. The liposome entrapped drug and the free drug were diluted in 5% dextrose in water as required to achieve the desired concentrations.

Nude mice were inoculated with the human colon cancer cell line HT-29 as described above in the methods section. Seventy mice were randomized to one of seven treatment groups as follows: free drug at 24 mg/kg, 15 mg/kg or 6 mg/kg; liposome entrapped drug at 24 mg/kg, 15 mg/kg or 6 mg/kg; saline. Treatment was initiated when average tumor volume was approximately 75 mm$^3$ on day 10 post-tumor inoculation. All treatments were administered as intravenous bolus injections given weekly for 3 treatments, specifically on days 10, 16 and 23.

Tumor size during and following each experiment was used as the primary evaluation of therapeutic efficacy. Body weight was evaluated to assess toxicity. All tumor bearing animals were observed following cessation of treatment, until euthanized based 25 on criteria above. Experiments were concluded when a majority of control tumors achieved the maximal allowed volume (4,000 mm$^3$).

Tumor size in each animal was measured repeatedly at various time points, thus these measurements were regarded as correlated information. Since the tumor sizes over time after treatment were of interest, repeated measurement analyses was done for each data set. By examining the data, a log transformation seemed reasonable. Let Y denote the original tumor measurement, let Z=log(Y+1). After transforming data, repeated measurement analyses was done for the transformed data Z. The SAS procedure PROC MIXED was used. The log growth rate for each treatment group was calculated and used to compare the different treatment groups. Statistical significance was declared at the 0.05 level, but due to multiple comparisons, adjustment to the type I error were done and a P-value of <0.0033 indicated a statistically significant difference in any designated comparison.

The results are summarized in Tables 1 and 2 and in FIGS. 2A–2B.

Example 3

Dose Finding Study for Liposome-entrapped MPE-Camptothecin

Liposomes containing entrapped MPE-camptothecin were prepared as described in Example 1. The liposome entrapped drug and the free drug were diluted in 5% dextrose in water as required to achieve the desired concentrations.

Nude mice were inoculated with the human colon cancer cell line HT-29 as described above in the methods section. Seventy mice were randomized to one of seven treatment groups as follows: liposome entrapped drug at 0.1 mg/kg, 0.5 mg/kg, 1 mg/kg, 3 mg/kg, 5 mg/kg or 20 mg/kg; and saline. Treatment was initiated when average tumor volume was approximately 75 mm$^3$ on day 9 post-tumor inoculation. All treatments were administered as intravenous bolus injections given weekly for 3 treatments, specifically on days 9, 16 and 23.

The tumor size was evaluated and analyzed as described in Example 2, and the results are shown in Tables 3 and 4 and in FIGS. 3A–3B.

Example 4

In Vivo Efficacy of Liposome-Entrapped Topotecan

A. Liposome Preparation

Liposomes containing topotecan were prepared as follows.

The lipids distearoylphospatidylcholine (DSPC) and (N-(carbonyl-methoxypolyethylene glycol 2000)-1,2- distearoyl-sn-glycero-3-phosphoethanolamine) (mPEG-DSPE) were combined at a molar ratio of 95:5 and dissolved in ethanol at 70° C. using continuous agitation. The lipid concentration in the ethanol solution was 8.9 grams per 10 mL ethanol.

Dextran sulfate-ammonium salt was prepared by ion exchange chromatography using dextran sulfate sodium salt as the starting material. A 100 mg/mL solution of dextran sulfate ammonium salt was prepared by dissolving dextran sulfate sodium salt in water and adjusting the solution pH to 5 using ammonium hydroxide.

100 mL of dextran sulfate solution was heated to 70° C. and combined with the ethanol solution of lipid while mixing to form oligolamellar liposomes. The temperature of the oligolamellar ethanol hydration liposome dispersion was maintained at 70° C. for one hour with continuous mixing.

The post hydration mixture was heated to 70 degrees and size reduced using a Lipex thermobarrel extruder through a series of polycarbonate membranes to arrive at a particle size near 100 nm mean particle diameter. Typically, the sequence involved 5 passes through an 0.2 µm pore diameter membrane, followed by 10 passes through an 0.1 µm pore diameter membrane.

Unentrapped dextran sulfate polymer and remaining ethanol were removed from the external bulk aqueous phase immediately prior to the active drug loading step with eight volume exchanges using 350 mM sodium chloride solution, followed by eight volume exchanges using a 10% sucrose solution. The diafiltration cartridge employed had a specified nominal molecular weight cutoff of 100,000 Daltons.

A solution of topotecan was prepared at a concentration of 2.5 mg/mL in 10% sucrose. The drug solution and diafiltered liposomes were combined at a volume ratio of 4:1, and the temperature of the resulting mixture was raised to 70° C. and maintained with constant stirring for one hour. Active drug loading was terminated by rapidly cooling the post-loading mixture using an ice water bath.

Unentrapped drug was removed by diafiltration employing a cartridge having nominal molecular weight cutoff of 100,000 Daltons. Typically, 8–10 volume exchanges were employed using 10% sucrose 10 mM Histidine pH 6.5 as the exchange buffer.

Drug concentration was adjusted to the final value by assaying for potency with a uv-vis absorbance measurement and diluting accordingly.

The final process step involved sterile grade filtration employing a 0.22 µm filter prior to filling vials.

B. Liposome Characterization

Percent encapsulation was determined using size exclusion chromatography to determine the percent drug in the void volume ("liposomal drug") to the total amount recovered in both the included and void volume fractions. Drug concentration was monitored using uv-vis absorbance spectrophotometry. Mean particle diameter was determined using quasielastic laser light scattering. Total lipid was determined using phosphorous assay. The results are summarized in the table below.

| Parameter | Liposome-entrapped Topotecan |
|---|---|
| total lipid | 17.2 mg/mL |
| total drug | 2.1 mg/mL |
| drug:lipid ratio (mol:mol) | 0.238 |
| mean particle diameter | 87.3 nm |
| percent encapsulation | 98.8 |

C. In Vivo Pharmacokinetics and Efficacy

Seventy two mice were inoculated with HT-29 cancer cells as described above in the methods section. Nine days after tumor inoculation, the animals were treated weekly with one of the following intravenous treatments: saline; liposome-entrapped MPE-camptothecin 4 mg/kg; free topotecan 25 mg/kg; liposome entrapped topotecan at drug dosages of 2 mg/kg, 5 mg/kg or 8 mg/kg. All treatments were administered as intravenous bolus injections given weekly for 3 treatments, specifically on days 9, 16 and 23.

Figure 5B:
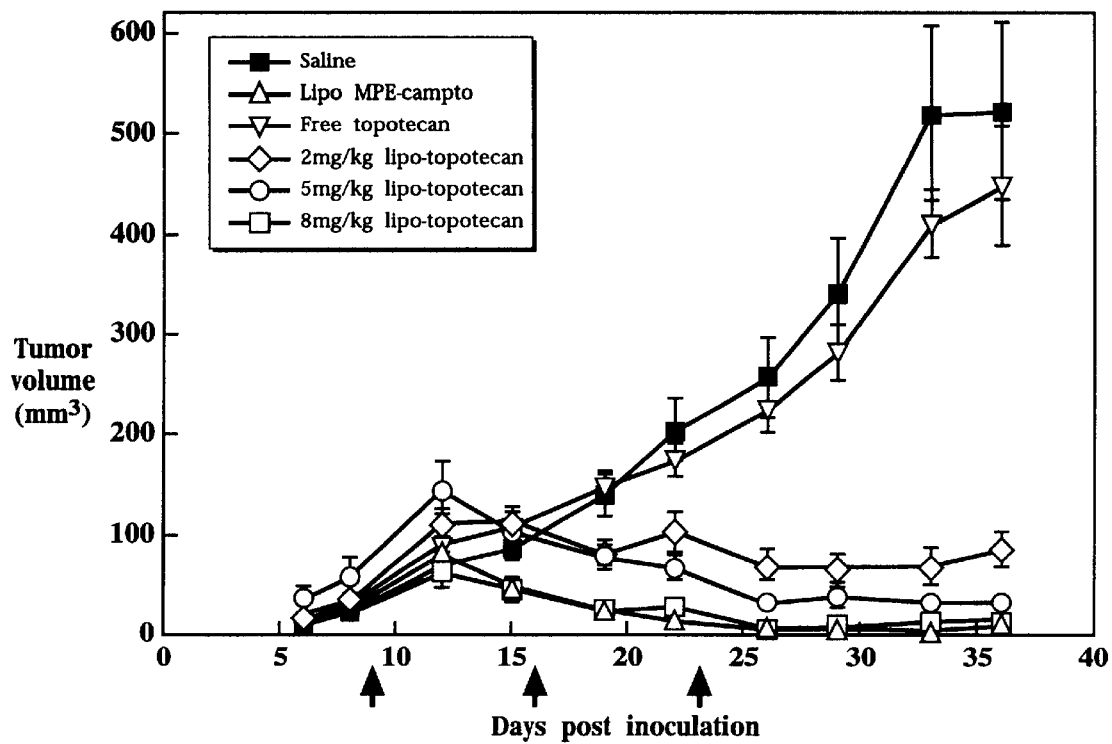
FIG. 5B is a plot showing tumor volume, in $mm^3$, as a function of days after inoculation with an HT29 colon tumor. The animals were treated on days 9, 16 and 23 after tumor inoculation with liposome-entrapped topotecan at dosages of 2 mg/kg (diamonds), 5 mg/kg (circles), 8 mg/kg (open squares); liposome-entrapped MPE-camptothecin at 4 mg/kg (triangles); free topotecan at a dose of 25 mg/kg (inverted triangles) and saline (closed squares)

The tumor size was evaluated and analyzed as described in Example 2, and the results are shown in Tables 6 and 7 and in FIGS. 5A–5B.

Example 5

In Vivo Efficacy of Liposome-Entrapped CKD-602

A. Liposome Preparation and Characterization

Liposomes containing CKD-602 were prepared as described in Example 4, except using a drug solution of CKD-602. The liposomes were characterized as described in Example 4 and the results are summarized below.

| Parameter | Liposome entrapped CKD-602 |
|---|---|
| total lipid | 12.5 mg/mL |
| total drug | 2.07 mg/mL |
| drug:lipid ratio (mol:mol) | 0.315 |
| mean particle diameter | 92.8 nm |
| percent encapsulation | 94.7 |

B. In Vivo Pharmacokinetics and Efficacy

Seventy two mice were inoculated with HT-29 cancer cells as described above in the methods section. Eleven days after tumor inoculation, the animals were treated weekly with one of the following intravenous treatments: saline, liposome-entrapped MPE-camptothecin 4 mg/kg; free CKD602 20 mg/kg; liposome entrapped CKD602 at drug dosages of 1 mg/kg, 2 mg/kg or 4 mg/kg. All treatments were administered as intravenous bolus injections given weekly for 3 treatments, specifically on days 11, 18 and 25.

The tumor size in each animal was measured twice weekly during the study to evaluate therapeutic efficacy. Body weight of each animal was monitored twice weekly to assess toxicity of the formulations. The results are shown in Tables 8 and 9 and in FIGS. 7A–7B.

Although the invention has been described with respect to particular embodiments, it will be apparent to those skilled in the art that various changes and modifications can be made without departing from the invention.

It is claimed:

1. A composition, comprising
   liposomes composed of at least about 20 mole percent of a vesicle-forming lipid and at least about 1 mole percent of a vesicle-forming lipid derivatized with a hydrophilic polymer, said polymer being distributed on both sides of the liposomes' bilayer membranes; and entrapped in the liposomes, a topoisomerase inhibitor at a concentration of at least about 0.10 μmole drug per μmole lipid, said liposomes having an inside/outside ion gradient sufficient to retain the topoisomerase inhibitor within the liposomes at the specified concentration.

2. The composition of claim 1, where the topoisomerase inhibitor is a topoisomerase I inhibitor selected from the group consisting of camptothecin and camptothecin derivatives.

3. The composition of claim 2, wherein the camptothecin derivative is selected from the group consisting of 9-aminocamptothecin, 7-ethylcamptothecin, 10-hydroxycamptothecin, 9-nitrocamptothecin, 10,11-methylenedioxycamptothecin, 9-amino-10,11-methylenedioxycamptothecin, and 9-chloro-10,11-methylenedioxycamptothecin.

4. The composition of claim 2, wherein the camptothecin derivative is selected from the group consisting of irinotecan, topotecan, (7-(4-methylpiperazinomethylene)-10,11-ethylenedioxy-20(S)-camptothecin, 7-(4-methylpiperazinomethylene)-10,11-methylenedioxy-20(S)-camptothecin and 7-(2-N-isopropylamino)ethyl)-(20S)-camptothecin.

5. The composition of claim 1, wherein the topoisomerase inhibitor is a topoisomerase I/II inhibitor selected from the group consisting of 6-[[2-(dimethylamino)-ethyl]amino]-3-hydroxy-7H-indeno[2,1-c]quinolin-7-one dihydrochloride, azotoxin and 3-methoxy-11H-pyrido[3',4'-4,5]pyrrolo[3,2-c]quinoline-1,4-dione.

6. The composition of claim 1, wherein the hydrophilic polymer is polyethyleneglycol having a molecular weight between 500–5,000 daltons.

7. The composition of claim 1, wherein the liposomes further include a vesicle-forming lipid having a phase transition temperature above 37° C.

8. The composition of claim 7, wherein the vesicle-forming lipid is selected from the group consisting of hydrogenated soy phosphatidylcholine, distearoylphosphatidylcholine and sphingomyelin.

9. The composition of claim 7, wherein the liposomes are comprised of between about 20–95 mole percent hydrogenated soy phosphatidylcholine and between about 1–20 mole percent distearoylphosphatidylethanolamine derivatized with polyethyleneglycol and between about 5–60 mole percent cholesterol.

10. The composition of claim 7, wherein the liposomes are comprised comprised of between about 30–65 mole percent hydrogenated soy phosphatidylcholine, between about 5–20 mole percent distearoylphosphatidylethanolamine derivatized with polyethyleneglycol, and between about 30–50 mole percent cholesterol.

11. The composition of claim 7, wherein the liposomes are comprised of between about 20–95 mole percent distearoylphosphatidycholine and between about 1–20 mole percent distearoylphosphatidylethanolamine derivatized with polyethyleneglycol.

12. The composition of claim 1, wherein the liposomes include a polyanionic polymer.

13. The composition of claim 12, wherein said polyanionic polymer is selected from the group consisting of dextran sulfate, chondroitin sulfate A, polyvinylsulfuric acid, and polyphosphoric acid.

14. The composition of claim 1, wherein the vesicle forming lipid is hydrogenated distearoylphosphatidycholine and the vesicle-forming lipid is distearoylphosphatidylethanolamine derivatized with polyethyleneglycol.

15. The composition of claim 14, wherein said vesicle-forming lipid and said derivatized lipid are present in a 95/5 molar ratio.

16. The composition of claim 1, wherein the anti-tumor activity of the liposome-entrapped topoisomerase inhibitor shows at least a four-fold increase over the anti-tumor activity of the drug in free-form.

17. The composition of claim 16, wherein the anti-tumor activity is measured using an HT-29 tumor model.

18. A composition for administration of a topoisomerase inhibitor, comprising liposomes composed of at least about 20 mole percent of a vesicle-forming lipid, said liposomes having an inside/outside ion gradient effective to retain the topoisomerase inhibitor within the liposomes; and entrapped in the liposomes, the topoisomerase inhibitor at a concentration of at least about 0.20 μmole drug per μmole lipid, wherein said liposome composition provides at least a four-fold increase in anti-tumor activity over the anti-tumor activity of the drug in free-form.

19. The composition of claim 18, wherein the toposiomerase inhibitor is a topoisomerase I inhibitor selected from the group consisting of MPE-camptothecin, topotecan, and (7-(2-N-isopropylamino)ethyl)-(20S)-camptothecin.

20. The composition of claim 18, wherein the toposiomerase inhibitor is a topoisomerase I/II inhibitor selected from the group consisting of 6-[[2-(dimethylamino)-ethyl]amino]-3-hydroxy-7H-indeno[2,1-c]quinolin-7-one dihydrochloride and 3-methoxy-11H-pyrido[3',4'-4,5]pyrrolo[3,2-c]quinoline-1,4-dione.

21. The composition of claim 18, wherein the liposomes further include a polyanionic polymer.

22. The composition of claim 18, wherein the anti-tumor activity is measured using an HT-29 tumor model.

23. A composition, comprising liposomes composed of at least about 20 mole percent of a vesicle-forming lipid and at least about 1 mole percent of a vesicle-forming lipid derivatized with a hydrophilic polymer, said polymer being distributed on both sides of the liposomes' bilayer membranes; and entrapped in the liposomes, 7-(2-(N-isopropylamino) ethyl)-(20S)-camptothecin at a concentration of at least about 0.10 μmole drug per μmole lipid, said liposomes having an inside/outside ion gradient sufficient to retain the topoisomerase inhibitor within the liposomes at the specified concentration.

24. The composition of claim 23, wherein the hydrophilic polymer is polyethyleneglycol having a molecular weight between about 500 Daltons and about 5,000 Daltons.

25. The composition of claim 23, wherein the liposomes further include a vesicle-forming lipid having a phase transition temperature above 37° C.

26. The composition of claim 25, wherein the vesicle-forming lipid is selected from the group consisting of hydrogenated soy phosphatidylcholine, distearoylphosphatidylcholine and sphingomyelin.

27. The composition of claim 23, wherein the liposomes are comprised of between about 20–95 mole percent hydrogenated soy phosphatidylcholine and between about 1–20 mole percent distearoylphosphatidylethanolamine derivatized with polyethyleneglycol and 5–60 mole percent cholesterol.

28. The composition of claim 23, wherein the liposomes are comprised of between about 30–65 mole percent hydrogenated soy phosphatidylcholine, between about 5–20 mole percent distearoylphosphatidylethanolamine derivatized with polyethyleneglycol and between about 30–50 mole percent cholesterol.

29. The composition of claim 23, wherein the liposomes are comprised of between about 20–95 mole percent distearoylphosphatidycholine and between about 1–20 mole percent distearoylphosphatidylethanolamine derivatized with polyethyleneglycol.

30. The composition of claim 23, wherein the vesicle forming lipid is hydrogenated distearoylphosphatidycholine and the vesicle-forming lipid is distearoylphosphatidylethanolamine derivatized with polyethyleneglycol.

31. The composition of claim 30, wherein said vesicle-forming lipid and said derivatized lipid are present in a 95/5 molar ratio.

32. The composition of claim 23, wherein the liposomes include a polyanionic polymer within the liposomes.

33. The composition of claim 32, wherein said polyanionic polymer is selected from the group consisting of dextran sulfate, chondroitin sulfate A, polyvinylsulfuric acid, and polyphosphoric acid.

34. The composition of claim 23, wherein the anti-tumor activity of the liposome-entrapped topoisomerase inhibitor shows at least a four-fold increase over the anti-tumor activity of the drug in free-form.

35. The composition of claim 34, wherein the anti-tumor activity is measured using an HT-29 tumor model.

36. A composition for administration of 7-(2-(N-isopropylamino)ethyl)-(20S)-camptothecin, comprising liposomes composed of at least about 20 mole percent of a vesicle-forming lipid, said liposomes having an inside/outside ion gradient effective to retain the 7-(2-(N-isopropylamino)ethyl)-(20S)-camptothecin within the liposomes; and entrapped in the liposomes, the 7-(2-(N-isopropylamino)ethyl)-(20S)-camptothecin at a concentration of at least about 0.20 µmole drug per mole lipid, wherein said liposome composition provides at least a four-fold increase in anti-tumor activity over the anti-tumor activity of the drug in free-form.

37. The composition of claim 36, wherein the hydrophilic polymer is polyethyleneglycol having a molecular weight between about 500 Daltons and about 5,000 Daltons.

38. The composition of claim 36, wherein the liposomes further comprise a vesicle-forming lipid having a phase transition temperature above 37° C.

39. The composition of claim 38, wherein the vesicle-forming lipid is selected from the group consisting of hydrogenated soy phosphatidylcholine, distearoylphosphatidylcholine, and sphingomyelin.

40. The composition of claim 36, wherein the liposomes are comprised of between about 20–95 mole percent hydrogenated soy phosphatidylcholine and between about 1–20 mole percent distearoylphosphatidylethanolamine derivatized with polyethyleneglycol.

41. The composition of claim 36, wherein the liposomes are comprised of 95 mole percent hydrogenated soy phosphatidylcholine and 5 mole percent distearoylphosphatidylethanolamine derivatized with polyethyleneglycol.

42. The composition of claim 36, wherein the liposomes further include a polyanionic polymer.

43. The composition of claim 42, wherein said polyanionic polymer is selected from the group consisting of dextran sulfate, chondroitin sulfate A, polyvinylsulfuric acid, and polyphosphoric acid.

44. The composition of claim 36, wherein the anti-tumor activity is measured using an HT-29 tumor model.

45. A method of treating a tumor in a subject, comprising preparing liposomes composed of at least about 20 mole percent of a vesicle-forming lipid and at least about 1 mole percent of a vesicle-forming lipid derivatized with a hydrophilic polymer chain, said polymer being distributed on both sides of the liposomes' bilayer membrane, said liposomes containing a topoisomerase inhibitor entrapped in the liposomes at a concentration of at least about 0.10 mole per µmole lipid, the liposomes having an inside/outside ion gradient sufficient to retain the topoisomerase inhibitor within the liposome at the specified concentration; and administering the liposomes to the subject.

46. The method of claim 45, wherein preparing further comprises entrapping the inhibitor in the liposomes by remote loading.

47. The method of claim 46, wherein entrapping further comprises entrapping the topoisomerase inhibitor in the liposomes using an ammonium sulfate gradient.

48. The method of claim 46, wherein entrapping further comprises entrapping the topoisomerase inhibitor in the liposomes using a polyanionic polymer trapping agent.

49. The method of claim 48, wherein said polyanionic polymer is selected from the group consisting of dextran sulfate, chondroitin sulfate A, polyvinylsulfuric acid, and polyphosphoric acid.

50. The method of claim 45, wherein preparing further includes preparing the liposomes with a vesicle-forming lipid having a phase transition temperature above 37° C.

51. The method of claim 50, wherein the vesicle-forming lipid is selected from the group consisting of hydrogenated soy phosphatidylcholine, distearoylphosphatidylcholine and sphingomyelin.

52. The method of claim 51, wherein the liposomes are comprised of 20–95 mole percent distearoylphosphatidylcholine and 1–20 mole percent distearoylphosphatidylethanolamine derivatized with polyethyleneglycol.

53. The method of claim 51, wherein the liposomes are comprised of 30–65 mole percent hydrogenated soy phosphatidylcholine, 5–20 mole percent distearoylphosphatidylethanolamine derivatized with polyethyleneglycol and 30–50 mole percent cholesterol.

54. The method of claim 51, wherein the liposomes are comprised of between about 20–95 mole percent hydrogenated soy phosphatidylcholine and between about 5–20 mole percent distearoylphosphatidylethanolamine derivatized with polyethyleneglycol.

55. The method of claim 54, wherein said hydrogenated soy phosphatidylcholine and said derivatized lipid are present in a 95/5 molar ratio.

56. The method of claim 45, whereby said administering is effective to achieve at least a east a four-fold increase in anti-tumor activity over the anti-tumor activity of the topoisomerase inhibitor in free-form.

57. The method of claim 56, wherein the anti-tumor activity is measured using an HT-29 tumor model.

* * * * *